(12) United States Patent
Homyk et al.

(10) Patent No.: US 10,871,503 B1
(45) Date of Patent: *Dec. 22, 2020

(54) METHODS FOR DEPTH ESTIMATION IN LASER SPECKLE IMAGING

(71) Applicant: Verily Life Sciences LLC, Mountain View, CA (US)

(72) Inventors: Andrew Homyk, Belmont, CA (US); Jason Donald Thompson, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 334 days.

This patent is subject to a terminal disclaimer.

(21) Appl. No.: 15/953,222

(22) Filed: Apr. 13, 2018

Related U.S. Application Data

(63) Continuation of application No. 14/722,096, filed on May 26, 2015, now Pat. No. 9,970,955.

(51) Int. Cl.
| | |
|---|---|
| *G01P 5/26* | (2006.01) |
| *A61B 5/026* | (2006.01) |
| *G01N 21/53* | (2006.01) |
| *A61B 5/00* | (2006.01) |
| *G01N 11/02* | (2006.01) |
| *G01N 11/00* | (2006.01) |

(52) U.S. Cl.
CPC .............. *G01P 5/26* (2013.01); *A61B 5/0075* (2013.01); *A61B 5/0261* (2013.01); *G01N 11/02* (2013.01); *G01N 21/53* (2013.01); *G01N 2011/008* (2013.01); *G01N 2201/0612* (2013.01)

(58) Field of Classification Search
CPC ....... G01P 5/26; A61B 5/0075; A61B 5/0261; G01N 11/02; G01N 21/53
See application file for complete search history.

*Primary Examiner* — Joanne M Hoffman
(74) *Attorney, Agent, or Firm* — McDonnell Boehnen Hulbert & Berghoff LLP

(57) ABSTRACT

Systems and methods are provided for detecting the depth, flow rate, and other properties of regions of blood flow in biological tissue by illuminating the biological tissue with beams of coherent light and detecting responsively emitted light. This includes detecting lights emitted from the tissue having a plurality of respective different exposure times. The relationship between the intensity of the received light and the exposure times is determined and used to determine the depth, flow velocity, or other properties of regions of flow within the biological tissue. This can include determining a spatial and/or temporal contrast of the received light intensity. Determining the depth of a region of flow can include comparing determined properties of light received from the tissue at two different polarizations. Determining the depth of a region of flow can include comparing determined properties of light received from the tissue at two different locations.

20 Claims, 11 Drawing Sheets

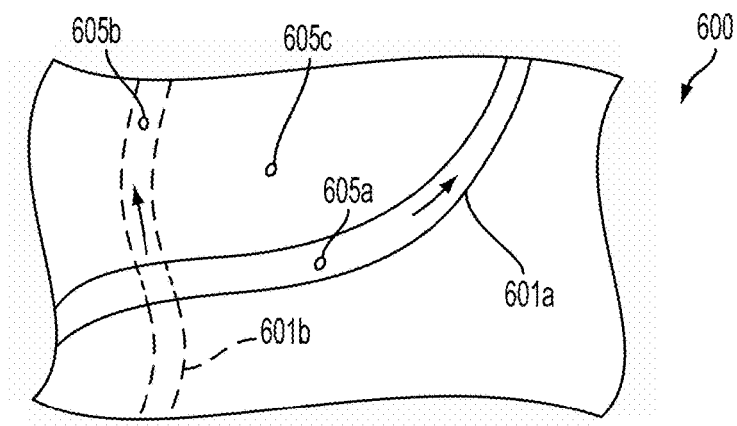
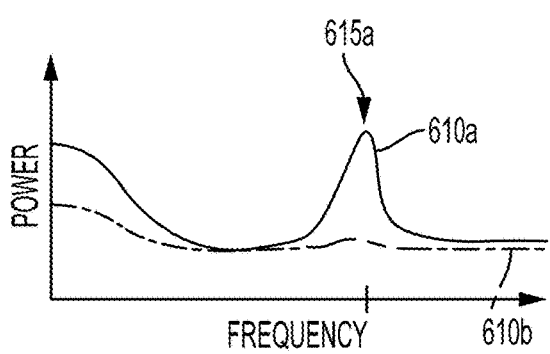 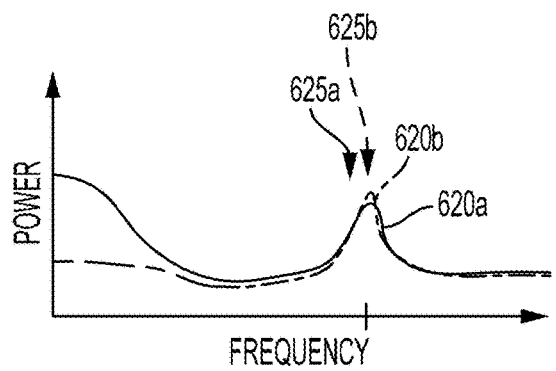
FIG. 6B  FIG. 6C
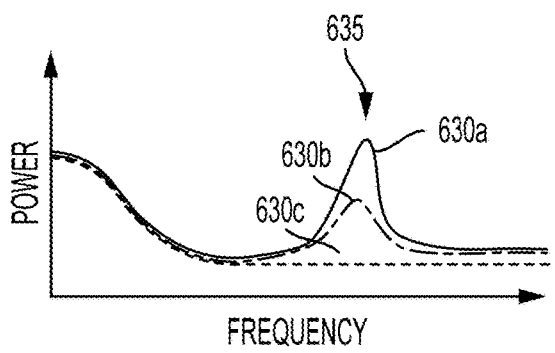 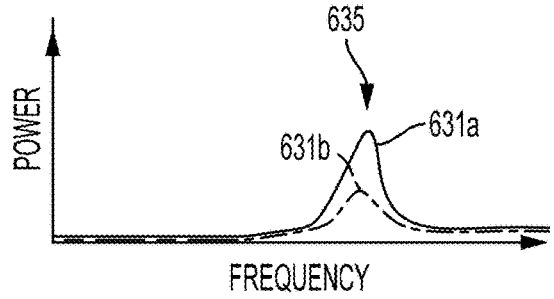
FIG. 6D  FIG. 6E

# METHODS FOR DEPTH ESTIMATION IN LASER SPECKLE IMAGING

CROSS-REFERENCE TO RELATED APPLICATION

This application claims priority to U.S. Non-Provisional patent application Ser. No. 14/722,096, filed May 26, 2015, which is incorporated herein by reference.

BACKGROUND

Unless otherwise indicated herein, the materials described in this section are not prior art to the claims in this application and are not admitted to be prior art by inclusion in this section.

Illumination of a scattering environment (e.g., an environment containing rough surfaces or other scattering objects or features) by a source of coherent, monochromatic light (e.g., a laser) can result in light emitted (i.e., reflected, refracted, diffracted, or otherwise scattered) from the environment forming a speckle pattern. That is, constructive and destructive interference between coherent, monochromatic light that takes different paths through the scattering environment due to scattering by features of the environment, and that thus experiences different path lengths, can form a pattern of light and dark speckles across a surface (e.g., a planar array of light sensors). The speckle pattern can be related to the features of the scattering environment, such as the specific geometry of a rough surface and the locations, orientations, and properties of individual scattering objects (e.g., blood cells) in the environment.

SUMMARY

Some embodiments of the present disclosure provide a method including: (i) during each of a plurality of time periods, each time period being associated with a respective exposure time: (a) emitting, by a light source, a beam of polarized coherent illumination into a biological tissue; (b) detecting, using at least one light sensor, an intensity of light of a first polarization received from a portion of the biological tissue during an exposure time; (c) detecting, using the at least one light sensor, an intensity of light of a second polarization received from the portion of the biological tissue during the exposure time; (ii) determining a first relationship between the detected intensities of light of the first polarization and the exposure times for the plurality of time periods; (iii) determining a second relationship between the detected intensities of light of the second polarization and the exposure times for the plurality of time periods; and (iv) determining a depth of a region of flow within the biological tissue based on the determined first relationship and the determined second relationship.

Some embodiments of the present disclosure provide a method including: (i) during each of a plurality of time periods, each time period being associated with a respective exposure time: (a) emitting, by a light source, a beam of coherent illumination into a biological tissue; (b) detecting, using at least one light sensor, an intensity of light received from a first portion of the biological tissue during an exposure time; (c) detecting, using the at least one light sensor, an intensity of light received from a second portion of the biological tissue during the exposure time; (ii) determining a first relationship between the detected intensities and the exposure times for the plurality of time periods for the first portion of the biological tissue; (iii) determining a second relationship between the detected intensities and the exposure times for the plurality of time periods for the second portion of the biological tissue; and (iv) determining a depth of a region of flow within the biological tissue based on the first determined relationship and the second determined relationship.

Some embodiments of the present disclosure provide systems configured to perform the above methods. Such systems could include wearable devices, medical and/or surgical imaging systems, or otherwise configured system or devices.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 6A is a top view of a biological tissue.

FIG. 6B illustrates frequency content determined from signals detected from the biological tissue of FIG. 6A.

FIG. 6C illustrates frequency content determined from signals detected from the biological tissue of FIG. 6A.

FIG. 6D illustrates frequency content determined from signals detected from the biological tissue of FIG. 6A.

FIG. 6E illustrates frequency content determined from the determined frequency content of FIG. 6D.

DETAILED DESCRIPTION

Figure 1:
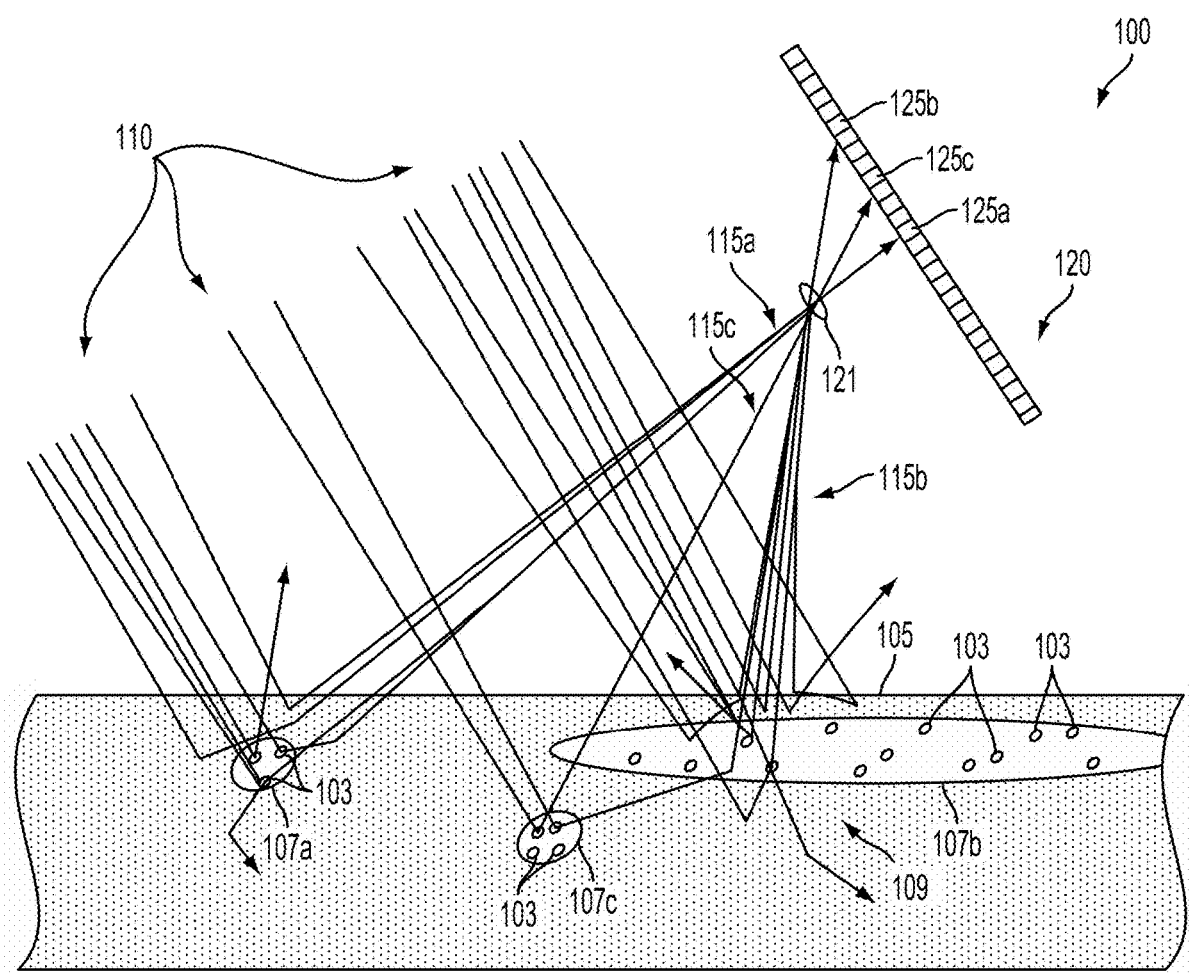
FIG. 1 is side partial cross-sectional view of an example system, while measuring properties of regions of flow in biological tissue.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where detection of flow properties (e.g., determining a map of flow properties across an area and/or within a volume) is desired. The environment may be any living or non-living body or a portion thereof, a gel, an emulsion, a fluid conduit, a fluid reservoir, etc. For example, one of skill in the art will recognize that the embodiments disclosed herein may be used to sense properties of fluid flow in a microfluidic system. Moreover, while the present disclosure describes embodiments for use in vivo, one of skill in the art will also recognize that in vitro applications are possible as well. Accordingly, the environment may also include a test tube or other vessel for holding a fluid.

I. Overview

The depth of a region of flow within an environment (e.g., a distance between a surface of the environment and the region of flow, e.g., a distance between the surface of a biological tissue and a region of blood flow in the biological tissue) can be detected by illuminating the environment using beams of substantially coherent, monochromatic light emitted by one or more light sources (e.g., lasers) and detecting the intensity (or other properties) of light emitted by the environment in response to the illumination. That is, scattering of the illumination by scattering elements in the environment (e.g., cells in blood, smoke particles in air) could cause the light responsively emitted from the environment to have one or more properties related to the movement of the scattering elements and/or to the location of those moving elements within the environment. A light sensor could be configured to detect the intensity (or some other property) of light emitted by the environment in response to the illumination and the detected intensity could be used to determine the velocity of the scatterers, the mean flow rate of fluid containing the scatterers, the depth of the scatterers within the environment, or some other information about the environment and/or the moving scattering elements therein.

Light emitted from, scattered from, or that has otherwise interacted with scatterers or other elements (e.g., blood cells) in a region of flow within an environment of interest (e.g., a biological environment containing flows of blood cells and other scatterers) can have one or more properties related to the depth of region of flow within the environment. For example, an amplitude, intensity, and/or magnitude of the light and/or some measure of the strength of a property of the light received from a region of flow (e.g., a magnitude of a peak of the power spectral density of the received light) could be reduced by increasing depth within the environment due to absorption of the light by material (e.g., tissue) of the environment that is intervening between the region of flow and a surface of the environment. Further, light that has interacted with deeper structures (e.g., deeper regions of flow) may have been scattered by or otherwise interacted with intervening elements of the environment more than light that has interacted with more shallow structures (e.g., portions of vasculature containing blood flows that are located on or near the surface of a biological tissue). The depth of a region of flow within an environment of interest (e.g., the depth of a portion of subsurface vasculature beneath a surface of a biological tissue) could be detected and/or determined by illuminating the environment of interest and detecting such properties of the responsively emitted light that are related to the depth of regions of flow with which the responsively emitted light has interacted (e.g., been reflected by, refracted by, scattered by, constructively and/or destructively interfered with, or otherwise optically interacted with).

In some examples, determining the depth of a region of flow within an environment could include detecting and/or determining one or more properties of the change over time and/or space of the light emitted from the environment responsive to coherent illumination. For example, information about the frequency content of the intensity of light received from a particular region of the environment could be related to a velocity and/or distribution of velocities of scatterers in a regions of flow, a depth and/or location of a region of flow, or some other property of the region of flow and/or its contents (e.g., an oxygen saturation of blood in a region of flow). Such frequency content could be determined by detecting the intensity of light received from a portion of the environment at a plurality of points in time (e.g., by detecting the intensity at a high sample rate). Additionally or alternatively, information about the frequency content of the light emitted from the environment and/or about some other property of the emitted light or a region of flow could be determined based on detecting the intensity of light received from the environment during a variety of different exposure times. A relationship between detected intensities of the emitted light and corresponding exposure times could be detected and/or determined for different emitted lights (e.g., lights emitted from different portions of the environment, emitted lights having different polarizations, emitted light having different wavelengths) and used to determine a depth of a region of flow within the environment or to determine other information about the environment (e.g., a flow velocity within a region of flow).

Detecting the intensity of light received from the environment during a variety of different exposure times could include integrating a detected intensity signal (e.g., by setting an integration time/period/duration for one or more elements of a charge-coupled device) during a plurality of different specified time periods having respective durations corresponding to the exposure times. Additionally or alternatively, detecting the intensity of light received from the environment during a variety of different exposure times could include illuminating the environment with a plurality of pulses of light having respective pulse widths corresponding to the exposure times. This could include modulating, over time, an amount of power provided to a light-producing element (e.g., a laser diode, a VCSEL, a pump laser or other cavity-pumping light emitter). Additionally or alternatively, illuminating the environment with a plurality of pulses of light could include operating a shutter (e.g., a liquid crystal shutter), an electronically actuated mirror or other electronically actuated optical element, a rotating wheel, or some other element(s) of a light source to modulate a level of light emitted from a light-emitting element (e.g., a laser) that is used to illuminate the environment. In some examples, detecting the intensity of light received from the environment during a variety of different exposure times could include summing (or performing some other calculation based on) two or more detected intensities to produce a determined intensity of light corresponding to a determined exposure time, e.g., to an exposure time substantially equal to a sum of the exposure times corresponding to the two or more detected intensities.

Determining a relationship between detected intensities of the emitted light and corresponding exposure times could include determining, for each exposure time based on detected intensities of light corresponding to each exposure time, a contrast value. A determined contrast value could be determined based on an amount of variation between intensities of light detected from a particular portion of the environment (e.g., using a particular pixel or other light-sensitive element of a light sensor) at a plurality of points in time (e.g., a temporal contrast). Additionally or alternatively, a determined contrast value could be determined based on an amount of variation between intensities of light detected from a number of portions of the environment (e.g., using a set of pixels or other light-sensitive elements of a light sensor), where the number of portions of the environment are proximate each other (e.g., a spatial contrast).

In some examples, a depth of a region of flow in the environment could be determined based on the polarization of the emitted light. For example, an environment of interest could be illuminated by linearly (or otherwise) polarized coherent light. Light responsively emitted from the environment that has interacted with deeper elements/regions of flow within the environment (e.g., that has been scattered more) could be less polarized (e.g., due to stochastic effects on the polarization of the light by each interaction with a scatterer or other element in the environment) than light that has interacted with shallower elements/regions of flow within the environment. First and second relationships between detected intensities of the emitted light of respective first and second different polarizations (e.g., orthogonal linear polarizations) and corresponding exposure times could be used to determine the depth of a region of flow within the environment. In some examples, this could include determining a ratio between determined features of the first and second determined relationships and/or some other information determined therefrom, e.g., a ratio between peaks of power spectral densities determined based on the intensity of the detected light of the different polarizations.

In some examples, a depth of a region of flow in the environment could be determined by comparing one or more detected or determined properties of light emitted from a portion of the environment containing the region of flow with one or more further portions of the environment that do not contain regions of flow. For example, light emitted from portions of the environment not containing regions of flow could be used as a baseline against which to compare light emitted from the portion of the environment containing the region of flow. First and second relationships between detected intensities of the emitted light of respective first and second different portions of the environment (e.g., a first portion containing and/or proximate to the region of flow and a second portion that does not contain and/or that is not proximate to a region of flow) and corresponding exposure times could be used to determine the depth of a region of flow within the environment. For example, the depth of a region of flow within an environment of interest could be determined based on a magnitude of a peak of a first power spectral density determined based on light from a first portion of the environment that contains and/or is proximate to the region of flow, where the magnitude of the peak is offset by a baseline magnitude determined from a corresponding peak of a second power spectral density determined based on light from a second portion of the environment that does not contain and/or that is not proximate to a region of flow.

The depth of regions of flow within an environment of interest could be determined for a plurality of portions and/or locations of the environment. Such determined depths could be improved by comparison with each other, e.g., based on information about the structure and/or distribution of regions of flow within an environment of interest. Further, such determined depths could be used to map structures (e.g., structures related to regions of flow) within the environment. For example, the location, depth, direction, length, pattern of branching, width, and/or other properties of portions of vasculature on and/or within a biological tissue could be determined based on a plurality of determined depths of regions of flow within the biological tissue. Such determined depths of regions flow could be used to map vasculature within a biological tissue, e.g., to provide information to plan and/or guide a surgical intervention.

The environment of interest could be any environment that, when illuminated by a laser or other source of substantially coherent light, emits light having one or more properties (e.g., a pattern of constructive and destructive interference (e.g., a speckle pattern), a degree of Doppler shift relative to a wavelength of illumination) related to the configuration of elements (e.g., scattering elements, blood cells) in the environment such that a change in the one or more properties can be related to a depth, location, flow rate, flow velocity, flow property, or other property of one or more regions of flow in the environment (e.g., a velocity of flow of a fluid in the environment). The environment could include gases, liquids, gels, or other fluids. The environment can include a population of scattering agents, i.e., small particles or other objects or features that can move within a region of flow and reflect, refract, diffract, or otherwise scatter light. In some examples, the environment could be a biological environment that includes blood cells, portions of vasculature, and other tissues. For example, the environment could be a biological tissue in a surgical environment that is subject to a surgical intervention, e.g., to an intervention that includes cutting, ablating, ligating, cauterizing, or otherwise manipulating or interacting with regions of the biological tissues according to an application.

In some embodiments, the above described methods for determination of the depth, flow velocity, or other properties of regions of flow within an environment could be performed by a stationary measurement device that may be brought into contact or proximity with a target environment. For example, the methods could be implemented by a system configured to emit one or more beams of coherent light toward a biological tissue undergoing a surgical intervention, and to determine depths or other properties of regions of flow (e.g., portions of surface and/or subsurface vasculature) within the biological tissue based on light responsively emitted from the biological tissue. Such determined depths could be used to map vasculature in the biological tissue, to detect the presence and/or location of a tumor in the biological tissue, or to determine some other information about the biological tissue. Such information could be presented (e.g., via a display, via an augmented reality device, via a control console of a robotic surgical system) to a surgeon. Additionally or alternatively, such information could be used to operate an automated or semi-automated robotic surgical system (e.g., to inform the ablation of a target tissue while avoiding causing damage to vasculature in the tissue). In some embodiments, the above described methods could be implemented by a wearable device configured to detect the depth or other properties of regions of flow (e.g., flow velocities) through the skin of a wearer, e.g., to determine a depth or other properties of portions of vasculature of a wearer. In other embodiments, the above described methods may be implemented by systems configured to interrogate an environment that is not a part of a human body, e.g., an in vitro or other sample container, an outdoor environment, an animal body, or some other environment of interest that can scatter or otherwise interact with emitted beams of coherent illumination in a manner related to properties of regions of flow within the environment.

It should be understood that the above embodiments, and other embodiments described herein, are provided for explanatory purposes, and are not intended to be limiting.

II. Illustrations of Scattering of Coherent Light in Biological Tissues

The location, depth, extent, flow properties (e.g., flow rates, flow velocities, distributions thereof), or other properties of regions of fluid flow or other regions of flow (e.g., solid regions in motion) in an environment can be detected by a variety of methods related to properties of the fluid or other materials in the region(s) of flow and of the environment. In examples wherein the environment contains scatterers (i.e., particles that can scatter incident illumination and that can be affected by or otherwise move with a region of flow in the environment), such properties (e.g., a depth, a mean flow velocity) of regions of flow of the environment could be detected and/or determined by illuminating the environment with coherent illumination and detecting a time- and/or space-dependence of a pattern, intensity, or other property of light responsively emitted from the environment. Such related properties of the responsively emitted light could be related to constructive and destructive interference between portions of the illumination that has been scattered by the scatterers in different ways related to the velocity, location, or other properties of the scatterers and/or other optical features of the environment.

FIG. 1 is a cross-sectional view through biological tissue 105 illustrating the operation of an example system 100. In the example shown in FIG. 1, the system 100 includes a laser (not shown) configured to emit a beam of coherent illumination 110 into the biological tissue 105 including portions of subsurface vasculature 107a, 107b, 107c (i.e., regions of flow) containing blood cells 103 (i.e., scatterers). The system 100 additionally includes an imager 120 comprising a plurality of light-sensitive elements (e.g., 125a, 125b, 125c) and an aperture 121 configured such that each light-sensitive element receives emitted light (e.g., 115a, 115b, 115c) from a respective portion of the biological tissue 105. For example, a first light-sensitive element 125a receives first emitted light 115a from a portion of the biological tissue 105 proximate to a first portion of vasculature 107a.

The system 100 additionally includes a controller (not shown) configured to operate the laser and the imager 120 to determine depths, flow properties (e.g., flow rates), or other properties of regions of flow (e.g., regions of blood flow contained by the portions of subsurface vasculature 107a, 107b, 107c) by detecting changing over time and/or over space of light emitted from the biological tissue 105 that has been scattered by blood cells or other scattering elements in the biological tissue 105. The system 100 could include further elements, e.g., a housing within which the laser, imager 120, and/or controller could be disposed, a mount configured to mount the laser and imager 120 to an arm or to other elements of anatomy of a person or to some surgical equipment or system, or to some other elements.

Emitted light (e.g., 115a, 115b, 115c) from the biological tissue 105 could include patterns of constructive and destructive interference related to individual portions of the beam of coherent illumination 110 being scattered by different scattering (e.g., reflecting, refracting, diffracting) elements in the biological tissue 105 (e.g., cell walls, blood cells, cell elements, tissue boundaries, chromophores, fat globules, or other reflective elements/boundaries and/or discontinuities in refractive index). Thus, different portions of the coherent illumination 110 experience different path lengths between emission at the laser and reception at a light-sensitive element (e.g., 125a, 125b, 125c) of the light sensor 120. The different portions of the beam of coherent illumination 110 (having been scattered toward the light sensor in the form of the emitted light 115a, 115b, 115c) are thus out of phase and will constructively and/or destructively interfere with each other in a manner related to respective amplitudes and relative phases of the portions of the emitted light (e.g., 115a, 115b, 115c) to form a pattern of constructive and destructive interference at the light sensor 120 and/or at other locations in the vicinity of the system 100 and biological tissue 105. Changes in the configuration of scatterers (e.g., blood cells) or other elements of the biological tissue 105 (e.g., compression or other deformations of the biological tissue 105, motion of the biological tissue 105 relative to the light source and/or imager 120) could cause changes over time in the pattern of light emitted from the biological tissue 105 that could be detected and used to determine properties of the biological tissue 105 (e.g., to determine a depth, flow velocity distribution, mean flow velocity, or other properties of a region of flow within the biological tissue 105).

As illustrated in FIG. 1, illumination 110 can be scattered multiple times before being emitted from or absorbed by the biological tissue 105. Such scattering can be caused by changes in refractive index or other scattering and/or reflective structures in the tissue, including cell walls, organelles within cells, artificial structures (e.g., nanoparticles) introduced into the tissue 105, or other elements of or within the biological tissue 105. As a result, light emitted from a particular portion of tissue may include light scattered from elements within the particular portion of tissue as well as light scattered by/within neighboring portions of tissue. Light emitted from the particular portion of tissue could be detected and used to determine information about the particular portion of tissue and/or portions of tissue neighboring the particular portion of tissue. For example, a time-varying pattern of constructive and destructive interference in light emitted from a particular portion of tissue could be detected (e.g., the intensity of light emitted from the portion of tissue during one or more periods of time could be detected) and used to determine a time-varying state (e.g., velocity) of scattering agents (e.g., blood cells) in the particular portion of tissue and/or in portions of tissue neighboring the particular portion of tissue.

As an illustrative example, FIG. 1 shows emitted light 115b emitted from a particular portion 109 of the biological tissue 105 that includes a second portion of vasculature 107b. Some of the emitted light 115b comprises light that is scattered only by elements within the particular portion of biological tissue 109. Additionally, some of the emitted light 115*b* comprises light that is scattered outside of the particular portion of biological tissue 109. For example, some of the emitted light 115*b* is scattered by blood cells 103 or other scattering elements (e.g., cell walls, organelles) disposed within the third portion of vasculature 107*c* before being emitted from the particular portion of biological tissue 109 toward the imager 120 (e.g., as the emitted light 115*b* that is received by a corresponding light-sensitive element 125*b*). Thus, changes in the biological tissue 105 that occur outside of the particular portion of biological tissue 109 (e.g., movement of blood cells in a blood flow within the third portion of vasculature 107*c*) could be related to a change in the intensity of emitted light 115*b* that is received by the corresponding light-sensitive element 125*b*.

Time-varying patterns of intensity of light received from a biological tissue (e.g., speckle events, spatial contrast) in light emitted from a particular portion of biological tissue could be related to changing properties of the particular portion of biological tissue, or of neighboring portions of tissue. The relationship between the time-varying patterns in the emitted light and the changing properties of a portion of tissue could be related to a depth of the tissue, a distance between the tissue and a surface via which the light is emitted, a coherence length and/or wavelength of illumination applied to the biological tissue, or some other properties of the biological tissues, the illumination applied to the tissues, and/or an imager or other sensor(s) used to receive light responsively emitted from the tissues.

Thus, time-varying patterns of the intensity of the emitted light (e.g., 115*a*, 115*b*, 115*c*) can be related to a configuration of elements of the biological tissue 105 (e.g., to the location of blood cells 103 in portions of subsurface vasculature 107*a*, 107*b*, 107*c* and/or interstitial spaces). The imager 120 detecting such time-varying patterns could include the imager 120 being configured and/or operated to detect any property or properties of emitted light (e.g., 125*a*, 125*b*, 125*c*) from the biological tissue 105 having a time dependence or other property that can be used to determine flow properties of blood or other fluids in the biological tissue 105. In some examples, this could include individual light-sensitive elements (e.g., 125*a*, 125*b*, 125*c*) of the imager 120 being configured to detect the intensity and/or some other property of the emitted light 117 at a plurality of points in time and/or during a plurality of different periods of time. For example, the intensity could be detected at a sufficiently high rate to detect the presence or other properties of individual speckle events or other short-duration features of the detected intensity.

Additionally or alternatively, information about time-varying patterns of the intensity of the received light could be detected by filtering, integrating, or otherwise performing some analog operations on light received by individual light-sensitive elements of the imager 120. For example, average intensities of the received light during a plurality of specified periods of time (e.g., during exposure times having respective specified durations) could be detected and used to determine flow properties in the biological tissue 105 (e.g., by determining a relationship between the exposure times and the variation of the intensities over time and/or space). This could include operating light-sensitive elements of the imager 120 to integrate or otherwise detect the intensity of the received light during one or more specified periods of time (e.g., during specified periods of time having respective durations corresponding to respective exposure times). Additionally or alternatively, an average intensity of the received light during specified periods of time could be detected by emitting, using the light source, pulses of light to illuminate the biological tissue during the specified periods of time.

In some examples, the imager 120 could be a camera (i.e., could include an aperture (e.g., 121), an array of light-sensitive elements (e.g., 125*a*, 125*b*, 125*c*), and/or optics) and detecting the intensity of light received from one or more portions of the biological tissue 105 during one or more specified periods of time could include detecting the intensity of the emitted light (e.g., 115*a*, 115*b*, 115*c*) that is received by the camera from various respective angles relative to the camera. Alternatively, the imager 120 could include a plurality of light-sensitive elements configured to receive light from respective portions of biological tissue by other means. In some examples, the individual light-sensitive elements could include baffles, coded apertures, diffraction gratings, angle-sensitive pixels (e.g., pixels of a planar Fourier capture array), or other elements configured such that individual light-sensitive elements receive light from a specified portion of tissue (e.g., at a specified angle(s) and/or specified location(s) relative to the light sensitive-element). Other configurations and operations of one or more imagers (e.g., 120) to detect the patterns of constructive and destructive interference in light emitted are anticipated.

Detecting time-varying patterns of the intensity of light emitted from the biological environment 105 (e.g., 115*a*, 115*b*, 115*c*) could include detecting a variety of properties of the patterns of the intensity of light of one or more different polarizations, wavelengths, or other different properties for one or more different portions of the biological environment. For example, the time-varying intensities of first and second lights having respective different first and second polarization (e.g., orthogonal linear polarizations) received from substantially the same portion of the biological tissue could be detected. Further, properties of the patterns of constructive and destructive interference in the received light could be detected and/or determined based on properties of an image formed by the received light (e.g., an image detected using the imager 120, an array of light-sensitive elements on a surface, or some other image-detecting apparatus). For example, a contrast ratio, a speckle location, a speckle size, a number of speckles, a speckle shape, an overall pattern width, or some other property or properties could be used to determine a depth, flow velocity, flow velocity distribution, or other properties of a region of flow within the biological tissue 105.

Figure 2:
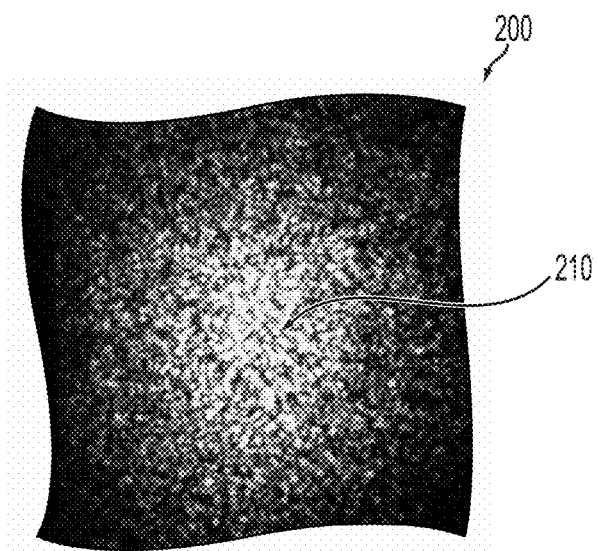
FIG. 2 is an example image of a speckle pattern emitted by a scattering medium that is illuminated by coherent light.

FIG. 2 illustrates an example speckle image 200 that could be generated on an imaging surface (e.g., a surface of the imager 120 on which light-sensitive elements, e.g., 125*a*, 125*b*, 125*c*, are disposed) in response to illumination of a scattering environment (e.g., the biological tissue 105, portions of subsurface vasculature 107*a*, 107*b*, 107*c*, blood cells 103) by light emitted from the environment (e.g., 115*a*, 115*b*, 115*c*) in response to a beam of coherent illumination (e.g., a beam 110 emitted by a laser). The speckle image 200 includes a plurality of speckles 210 corresponding to where (e.g., the locations of one or more particular pixels) the constructive and destructive sum of the light impinging on a corresponding region of the imaging surface results in an overall higher level of light intensity than in other regions of the speckle image 200.

Properties of the patterns of constructive and destructive interference that result in the speckle image 200 are related to properties of the scattering environment (e.g., location and/or depth of scattering elements in the environment, refractive index of elements of the environment), properties of the illuminating beam of coherent illumination (e.g., a wavelength, a spectral line width, an intensity, a coherence length, a beam width, a beam polarization), and of the imaging surface (and/or of apertures, optics, or other elements of an imager 120 comprising such a surface) on which the speckle image 200 is formed (e.g., the location of the imaging surface relative to the beam of coherent illumination and relative to the environment). Thus, time-dependent changes in the configuration of the environment (e.g., movement of scatterers in a fluid flow in the environment) could result in a time-dependent change in the patterns of constructive and destructive interference in the light emitted by the environment that could further result in a time-dependent change in the imaged speckle pattern 200. That is, the location, number, size, shape, intensity, or other properties of speckles 210 or other features of the speckle pattern 200 could change in a time-dependent manner related to a change in the environment and/or a change in the location of the imaging surface and/or source of the beam of coherent illumination relation to the environment.

The patterns of constructive and destructive interference represented by the speckle image 200 could be related to reflection, refraction, diffraction, scattering, absorption, or other interactions between a beam of coherent light illuminating an environment and elements of the environment. For example, interfaces between regions of the environment having different indices of refraction (e.g., at a cell wall, at a wall of an organelle or other cellular contents, at the wall of a portion of vasculature, at the surface of a bone, at the surface of a muscle, at a skin surface, at some other interface in a biological or other environment) can cause scattering, refraction, reflection, and/or other interactions with light. Other elements of an environment (e.g., metallic and/or semiconductive particles, surfaces, or other elements) could cause reflection, scattering, and/or other interactions with illuminating light in a manner related to the patterns of constructive and destructive interference represented by the speckle image 200.

FIGS. 3A-3D illustrate the operation of an example system 300 that could be operated to determine the location, extent, depth, flow properties (e.g., flow velocity, distribution of flow velocities), or other properties of regions of flow within an arm 305, e.g., of flowing blood in a portion of subsurface vasculature 307 in the arm 305. The system 300 includes a laser 310 configured to emit a beam of coherent illumination (a portion of which is illustrated as illumination 315) into tissue of the arm 305 that includes the portion of subsurface vasculature 307 and blood cells (e.g., illustrative blood cell 309) contained in the portion of subsurface vasculature 307 that move along with flowing blood in the portion of subsurface vasculature 307. The system 300 additionally includes an imager that includes an aperture 321 and a particular light-sensitive element 320 configured to detect the intensity or other properties (e.g., degree and/or direction of polarization) of a portion of the beam of coherent illumination 315 that is scattered by tissue of the arm 305 and that is emitted as emitted light (e.g., 317a-c) toward the imager such that the emitted light 317a-c is received by the particular light-sensitive element 320. The imager could additionally include a plurality of additional light-sensitive elements (e.g., formed as part of a CCD, CMOS active-pixel sensor (APS) array, or other light-sensitive structure with the particular light-sensitive element 320) configured to receive light from a plurality of respective locations of the arm 305 and/or from respective angles relative to the imager. The system 300 additionally includes a controller (not shown) configured to operate the laser 310 and the imager to determine the location, depth, flow properties (e.g., flow velocity), or other properties of flowing blood in the portion of subsurface vasculature 307 and/or other regions of flow within the arm 305. The system 300 could include further elements, e.g., a housing within which the laser 310, imager, and/or controller could be disposed, a mount configured to mount the laser 310 and light sensor 320 to the arm 305, or some other elements.

Figure 3A:
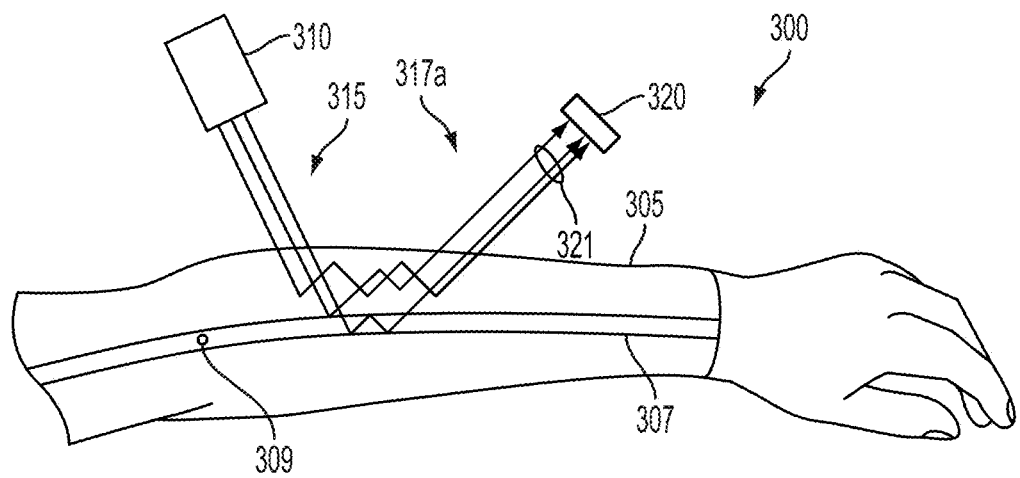
FIG. 3A is side partial cross-sectional view of an example system, while measuring regions of blood flow in a human arm.
Figure 3B:
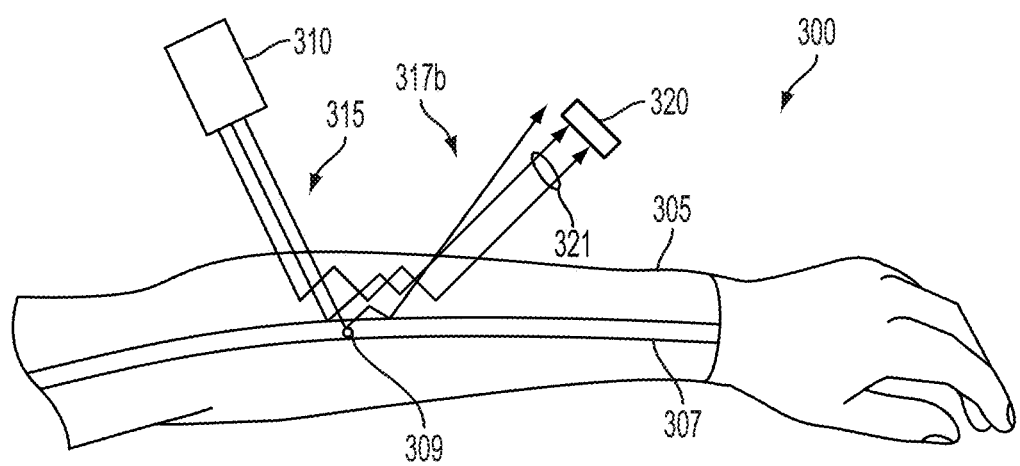
FIG. 3B is side partial cross-sectional view of the example system illustrated in FIG. 3A, while measuring regions of blood flow in a human arm.
Figure 3C:
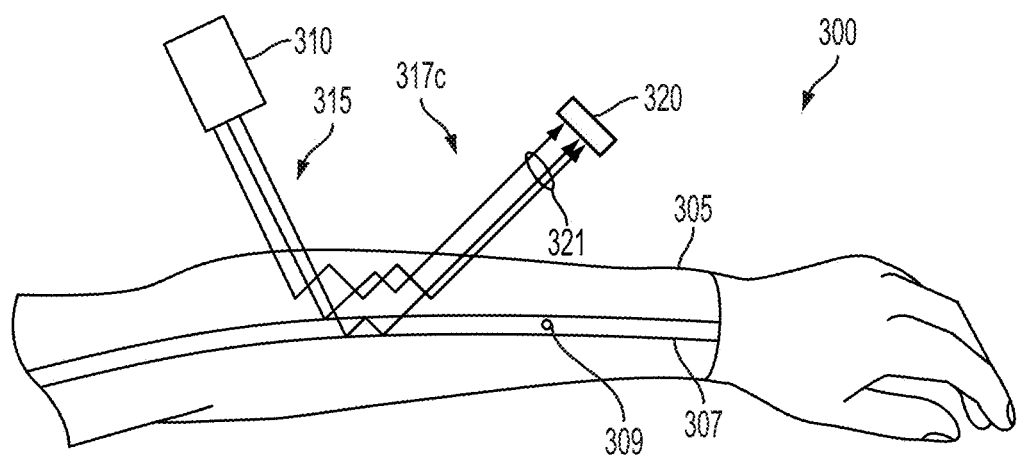
FIG. 3C is side partial cross-sectional view of the example system illustrated in FIG. 3A, while measuring regions of blood flow in a human arm.

To illustrate the operation of the system 300, the movement of an illustrative blood cell 309 due to the flow of blood in the portion of subsurface vasculature 307 is illustrated in FIGS. 3A-3C and the corresponding time-dependent changes of the pattern of constructive and destructive interference detected by the particular light-sensitive element 320.

FIG. 3A illustrates the system 330 and arm 307 during a first period of time. The illustrative blood cell 309 is in an upstream region of the portion of subsurface vasculature 307 that is substantially outside of a region illuminated by the illustrated coherent illumination 315. As a result, the particular light-sensitive element 320 detects a first light intensity related to a pattern of constructive and destructive interference in first emitted light 317a.

FIG. 3B illustrates the system 330 and arm 307 during a second period of time. The illustrative blood cell 309 is moved downstream due to blood flow into the region of the portion of subsurface vasculature 307 that is illuminated by the illustrated coherent illumination 315 and thus acts to scatter the illustrated coherent illumination 315. As a result, the particular light-sensitive element 320 detects a second light intensity related to a pattern of constructive and destructive interference in second emitted light 317b that is substantially different from the pattern of constructive and destructive interference in first emitted light 317a.

FIG. 3C illustrates the system 330 and arm 307 during a third period of time. The illustrative blood cell 309 is moved downstream due to blood flow into a downstream region of the portion of subsurface vasculature 307 that is substantially outside of the region illuminated by the illustrated coherent illumination 315. As a result, the particular light-sensitive element 320 detects a third light intensity related to a pattern of constructive and destructive interference in third emitted light 317c that is substantially similar to the pattern of constructive and destructive interference in first emitted light 317a.

The movement of the illustrative blood cell 309 through the portion of subsurface vasculature 305 during and between the first, second, and third periods of time (as illustrated in FIGS. 3A-C, respectively) results in the particular light-sensitive element 320 generating a speckle event in a detected light intensity waveform output by the light-sensitive element 320. The speckle event could be a trapezoidal pulse that includes a rising edge, a plateau, a falling edge, or other features that could be detected. One or more of these waveform elements could be related to the speed of the illustrative blood cell 309 and thus to a flow property in the biological tissues of the arm 305 (e.g., of the blood in the portion of subsurface vasculature 307). For example, the rate of increase in intensity during a rising edge of a trapezoidal pulse could correspond to the velocity of the illustrative blood cell 309 such that higher rates correspond to higher velocities.

Note that the movement of the illustrative blood cell 309 and the corresponding described trapezoidal pulse in an output light intensity waveform are meant as illustrative examples. A portion of subsurface vasculature could include many blood cells having respective different velocities related to the movement of blood in the portion of subsurface vasculature that could be related to respective changes/ contents of a received intensity of light. Further, the movement of an individual blood cell through a region of subsurface vasculature illuminated by a coherent light source could result in no speckle event, multiple speckle events, a speckle event that is a shape other than a trapezoidal pulse, or some other feature(s) to be present in a detected light intensity waveform or other detected signal related to the pattern of constructive and destructive interference in a portion of a beam of coherent illumination that is scattered in the environment including the portion of subsurface vasculature and blood cell(s)) and that is emitted as an emitted light toward a light sensor.

Further, note that, due to multiple scattering of light in biological tissues of the arm 305, properties (e.g., speckle events) of a detected light intensity could be due to interaction with scatterers or other elements in portions of biological tissue proximate to the region illuminated by the illustrated coherent illumination 315 and/or due to interaction with scatterers or other elements in neighboring portions of biological tissue (e.g., regions illuminated by other portions of a beam of coherent illumination emitted by the laser 310). Conversely, changes in the pattern of constructive and destructive interference in light emitted from the biological tissue that are related to motion or changes of a particular blood cell or other scatterer (e.g., 309) could result in changes (e.g., speckle events) in the time-varying pattern of illumination received by other light-sensitive elements (not shown) of a light sensor (e.g., pixels of a camera that includes the particular light-sensitive element 320).

Figure 3D:
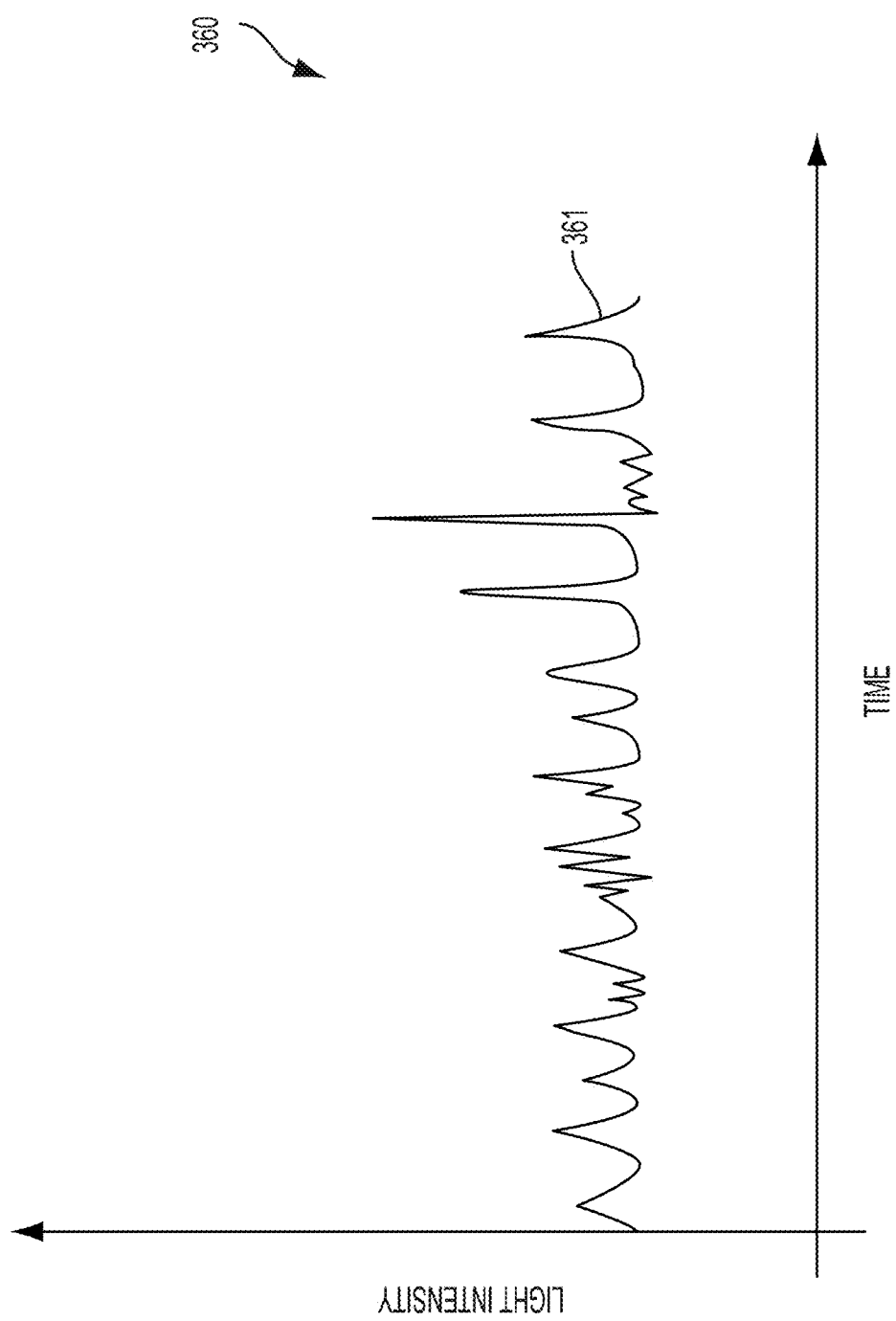
FIG. 3D is an example output generated by the example system illustrated in FIGS. 3A-3C.

FIG. 3D shows an example light intensity waveform 361 of light that could be received by the system 300 when a plurality of blood cells and other scatterers are being moved in a flow of blood or other region of flow in the arm 305. The light intensity waveform 361 includes a plurality of speckle events having respective shapes, durations, amplitudes, rise/fall times, and/or other properties. The system 300 could include electronics (e.g., amplifiers, filters, comparators, envelope detectors, slope detectors, differentiators, peak detectors, ADCs, microprocessors, microcontrollers) configured to determine one or more flow properties in biological tissue of the arm 305 (e.g., of the blood in the portion of subsurface vasculature 307) based on one or more detected properties of the light intensity waveform 361. For example, the electronics could be configured to detect and sample the light at a specified sufficiently high rate such that a rise time of individual speckle events in the light intensity waveform 361 could be determined and used to determine a corresponding blood cell velocity. The specified high rate of sampling could be related to the duration, frequency, or some other temporal property of the light intensity waveform 361 (e.g., an expected minimum duration of speckle events). For example, a speckle event could be expected to last approximately 1 microsecond, so the specified sample rate could be sufficiently in excess of 1 megahertz to resolve features of interest (e.g., a rising edge, a plateau, a falling edge) of individual speckle events. The electronics could be further configured to determine a distribution of velocities of individual blood cells in the blood or other fluid, a mean flow rate of the blood or other fluid, and/or some other flow property of the blood or other fluid in the biological tissues of the arm 305.

Note that features of the example light intensity waveform 361 illustrated in FIG. 3D are meant as illustrative examples of signals related to time-varying patterns of constructive and destructive interference in light emitted from an environment of interest that could be used to determine a depth, location, flow properties (e.g., mean flow velocity), or other properties of regions of flow within the environment. Rise times, rise rates, pulse widths, fall times, fall rates, event frequencies and other temporal features of such detected signals are non-limiting examples of time-dependent waveform features that could be related to and/or detected and used to determine properties of regions of flow within an environment. Additionally or alternatively, an envelope, a spectrum, a power spectral density, a derivative, a power in one or more frequency bands, an autocorrelation, or some other time-dependent variable or variables related to such detected signals could be used to determine properties of regions of flow within an environment.

A variety of properties of the time-varying intensity (e.g., 361) of light emitted from a biological tissue in response to illumination by coherent light could be related to properties of regions of flow within the biological tissue. For example, a power spectral density or other frequency-related properties of the intensity waveform could be related to a depth, flow velocity, flow velocity distribution, or other properties of a region of flow. For example, higher velocity flows could result in shorter and/or more frequent speckle events and/or could otherwise increase a power of the intensity waveform at higher frequencies (e.g., could be related to a higher center frequency of a peak in a power spectral density of the intensity waveform). Properties of a peak or other feature in the power spectral density of the intensity waveform could be related to the distribution of velocities of scatterers in a region of flow from which the emitted light was emitted and/or with which the emitted light has interacted. For example, a center frequency and shape of such a peak could be related to a mean velocity and velocity distribution of scatterers (e.g., blood cells) in the region of flow (e.g., portion of subsurface vasculature). Further, an amplitude of such a peak could be related to the depth of the region of flow. For example, light that has been scattered by or that has otherwise interacted with deeper regions of flow could be absorbed more and/or scattered more by intervening tissues of the biological tissue than light that has been scattered by or that has otherwise interacted with shallower regions of flow. Thus, the amplitude of a peak in a power spectral density determined based on the intensity of light received from deeper regions of flow could be less than the amplitude of a corresponding peak in a power spectral density determined based on the intensity of light received from shallower regions of flow.

Such frequency information (e.g., power spectral density) or other information about the time-varying intensity of light received from a biological tissue could be detected and/or determined in a variety of ways. In some examples, the time-varying intensity of light received from a particular portion of the biological tissue could be detected at a specified sufficiently high rate such that the power spectral density or other information about the time-varying intensity of the light could be determined based on the detected samples of the intensity and used to determine a depth, mean flow velocity, or other properties of regions of flow proximate to the particular portion of the biological tissue. Additionally or alternatively, information about the time-varying intensity of the received light could be determined based on detecting the intensity of the received light during a plurality of different exposure times and determining a relationship between the detected intensities and the corresponding exposure times. In some examples, this could include determining a contrast or some other measure of the variability of the detected intensities (e.g., across a number of intensities detected at respective different points in time from a particular portion of the biological tissue, across a number of intensities detected from a plurality of different proximate portions of the biological tissue) for each of the different exposures.

The laser 310 could be configured in a variety of ways and include a variety of elements such that the emitted beam of coherent illumination (e.g., illustrated portion of coherent illumination 315) has one or more specified properties according to an application. The beam of coherent illumination could have a specified wavelength. In some examples, the wavelength of the beam of coherent illumination could be specified such that it could penetrate an environment of interest, be scattered by scatterers in a fluid flow(s) in the environment of interest, or according to some other considerations. For example, the environment could include portions of vasculature within a portion of human anatomy (e.g., within a portion of tissue targeted for a surgical intervention) and the wavelength of the beam of coherent illumination could be between approximately 400 nanometers and approximately 1000 nanometers. In some examples, the wavelength of the beam of coherent illumination could be specified relative to a characteristic size or other property of scatterers (e.g., blood cells, cavitation bubbles, natural and/or artificial particles, bubbles or gas or other material having dissimilar optical properties to a surrounding fluid medium) such that the scatterers could scatter the beam of coherent illumination and cause the environment to emit light having time-varying patterns of constructive and destructive interference and/or time-varying patterns of intensity related to the configuration of the environment and/or scatterers (e.g., related to the depth and/or motion of the scatterers within regions of flow within an environment). The wavelength of the beam of coherent illumination could be within a near-infrared (NIR) transparency window of biological tissue (e.g., between approximately 780 and approximately 810 nanometers).

In some examples, the beam of coherent illumination could have a coherence length that is greater than some minimum coherence length (e.g., greater than 1 millimeter) that is related to scattering properties of elements of the environment (e.g., skin cells, connective tissue, portions of subsurface vasculature, blood cells, and other elements of biological tissues of a portion of human anatomy). The specified minimum coherence length could be related to a spacing of scatterers or other optical features (e.g., reflecting, refracting, and/or diffracting interfaces between regions having different indices of refraction, metallic and/or semiconductive elements) in the environment such that one or more properties of time-varying patterns of constructive and destructive interference can be detected and used to determine a depth, location, flow property, or other properties of a region of flow in the environment. Additionally or alternatively, the specified minimum coherence length could be related to a range of expected path lengths of scattered light through the environment. Further, the laser 310 could include a volume holographic grating, a monochromator, a Lyot filter, a distributed Bragg reflector, a dielectric mirror, or some other element(s) configured to increase a coherence length of and/or decrease a spectral line width of the beam of coherent illumination. Such elements could be disposed on a discrete laser (e.g., a volume holographic grating could be disposed in the path of the beam of a laser) and/or could be incorporated into one or more elements of the laser 310 (e.g., mirrors, lenses, gain media, frequency doublers, or other elements of the laser 310 could be configured such that they had properties of one or more of the listed additional elements).

The laser 310 could be selected from a wide variety of lasers according to an application. The laser 310 could include a gas laser, a chemical laser, a dye laser, a metal-vapor laser, a solid-state laser, a semiconductor laser, or any other type of laser configured to produce a beam of coherent illumination having one or more specified properties (e.g., wavelength, spectral line width, coherence length, beam width, beam dispersion) such that the laser could illuminate an environment of interest (e.g., a portion of subsurface vasculature 307, tissues undergoing a surgical intervention) that contains light-scattering elements (e.g., blood cells, human tissue) disposed in regions of flow such that the environment of interest responsively emits light having time-varying patterns of constructive and destructive interference that have one or more time- and/or space-dependent properties that can be detected and used to determine a depth, location, flow properties (e.g., a flow velocity of blood within a particular portion), or other properties of regions of flow within the environment. In some examples, the coherence length of coherent light emitted by the laser and/or emitted by the system after being passed through one or more filters (e.g., monochromators, volume holographic gratings) could be specified to be greater than some minimum coherence length (e.g., approximately 100 millimeters) to enable detection of properties of regions of flow within a range of depths within a biological tissue (e.g., within approximately 3 to approximately 5 millimeters of the surface of a biological tissue).

In some applications, the system 300 could be a wearable device and the laser 310 could be configured to satisfy limited power and space requirements of the wearable device such that the system 300 could be battery-powered and could be comfortably worn by a wearer (e.g., worn around a wrist of the wearer). The system 300 could be configured to be operated in a surgical environment (e.g., in connection with a variety of additional surgical instruments and/or imaging devices) and one or more elements of the system 300 could be configured to perform some additional function(s). For example, the laser 310 could additionally be configured to ablate biological tissue (e.g., by producing a beam of illumination of sufficient power to vaporize, cauterize, coagulate, ablate, or otherwise irreversibly alter biological tissue) and/or to control a direction of the emitted beam of coherent illumination (e.g., by being optically coupled to one or more actuated mirrors or other actuated elements).

In some examples, the laser 310 could be a small laser diode, e.g., a VCSEL, a double heterostructure laser, a quantum well laser, or some other structure of semiconductor laser incorporating gallium nitride, indium gallium nitride, aluminum gallium indium phosphide, aluminum gallium arsenide, indium gallium arsenide phosphide, lead salt, or some other material or combination of materials as a gain medium. In some examples, the laser 310 could include a stabilized fiber laser. In some examples, the laser 310 could include frequency doublers, optics, collimators, or some other elements according to an application. In some examples, the laser 310 could be incorporated into other elements of the system 300. For example, the laser 310 could be wire-bonded, soldered, or otherwise electronically and/or mechanically coupled to a circuit board or other element(s) of the system, 300. Additionally or alternatively, the laser 310 or elements thereof could be incorporated into a single semiconductor device (e.g., wafer or chip) with other components (e.g., a laser power supply, a microcontroller). Further, the laser 310 could be configured to control the direction of the beam of coherent illumination 315 (e.g., by including servos, motors, piezo elements, or other actuators configured to translate and/or rotate the laser and/or optics or other elements thereof) to enable detection of properties of regions of flow in specified sub-regions of the arm 305 by directing the beam of coherent illumination toward the different specified sub-regions of the arm 305.

In some examples, the system 300 could include more than one laser. Individual lasers of the more than one laser could have respective specified properties (e.g., locations, angles and/or locations of emitted beams of coherent illumination, wavelengths, coherence lengths, polarizations) according to an application. More than one laser could be provided to allow for detection of properties (e.g., depth, flow velocity) of regions of flow in more than one region of the arm 305 (e.g., portions of tissue at multiple depths other and/or locations in the arm 305). In some embodiments, the system 300 could include a spatially distributed array of lasers configured such that individual lasers of the array emit beams of coherent illumination into respective individual sub-regions (e.g., overlapping or non-overlapping portions of tissue) of the arm 305. Such an array of lasers could be operated to determine properties of regions of flow within the respective individual sub-regions of the arm 305 (e.g., to determine a flow map within the arm 305, to determine a depth, location, shape or other property of vasculature in the arm 305, or according to some other application). More than one laser could be provided to enable higher-accuracy or otherwise improved detection of a depth, location, extent, flow property, or other property of blood, interstitial fluid, or some other fluid (e.g., by providing a redundant source of coherent illumination, by allowing illumination of a portion of biological tissue from multiple angles, by providing multiple wavelengths of illumination for detection).

Further, the use of multiple lasers to illuminate multiple portions of a biological tissue could allow for detection of properties of regions of flow in multiple portions of the biological tissue by a reduced set of light-sensitive elements (e.g., by a single light-sensitive element). For example, the imager could include a single light-sensitive element (or a small set of light-sensitive elements) configured to receive light from a plurality of portions of a biological tissue, and one or more lasers could illuminate individual portions of the plurality of portions of the biological tissue during respective periods of time. A plurality of time-varying patterns of intensity of light detected by the single light-sensitive element during respective periods of time could be used to determine properties of regions of flow in respective individual portions of the plurality of portions of the biological tissue. One or more lasers illuminating a plurality of portions of the biological tissue could include operating a plurality of lasers configured to emit beams of coherent illumination toward respective portions of the biological tissue. Additionally or alternatively, one or more lasers could be configured to control a direction and/or location of an emitted beam of illumination to illuminate specified portions of the biological tissue (e.g., by being coupled to one or more actuated mirrors or by being otherwise configured to control a direction of an emitted beam of coherent illumination).

The imager (including particular light-sensitive element 320) could include a variety of light-detecting apparatus configured to detect the intensity or other properties (e.g., degree and/or direction of polarization) of light that is emitted by an environment (e.g., 305, 307) and that is related to the configuration of the environment and/or scatterers therein. The imager (including, e.g., particular light-sensitive element 320) could include one or more photodetectors, photodiodes, phototransistors, CCDs, active pixel sensors, angle-sensitive pixels, photoresistors, or other light-sensitive elements. The particular light-sensitive element 320 and/or other light-sensitive elements of the imager could be configured to detect an intensity, a wavelength, a spectrum, a degree of polarization, a direction of polarization, or some other property of light emitted by the environment and received at one or more locations on or within the imager. For example, light-sensitive elements of the imager could be configured to detect the intensity of light received from respective specified regions of the arm 305 that are received from respective directions relative to the imager. In some examples, the imager could comprise a camera (i.e., including, e.g., aperture 321, a plurality of particular light-sensitive elements 320, and/or optics).

Note that the imager being configured as a camera (that is, including an aperture 321, one or more light-sensitive elements 320, and/or other optical elements configured such that individual light-sensitive elements receive light from respective directions relative to the imager) is meant as a non-limiting example. In other examples, the imager could include a plurality of light-sensitive elements configured to receive light from respective portions of biological tissue by other means. In some examples, the individual light-sensitive elements could include baffles, coded apertures, diffraction gratings, angle-sensitive pixels (e.g., pixels of a planar Fourier capture array), or other elements configured such that individual light-sensitive elements receive light from a specified portion of tissue (e.g., at a specified angle(s) and/or specified location(s) relative to the light sensitive-element). Other configurations and operations of one or more imagers to detect the patterns of constructive and destructive interference in light emitted are anticipated.

The imager and/or light-sensitive elements thereof (e.g., 320) could include a variety of components according to an application. The imager could include lenses, polarization filters, color filters, apertures, mirrors, diffraction gratings, liquid crystal elements, baffles, or other optical elements to affect the light received by the imager and/or by particular light-sensitive elements thereof. In some examples, the imager could include a color filter configured to substantially block light having wavelengths different from a wavelength of light emitted by the laser 310. In some examples, the size of specified regions from which individual light-sensitive elements of the imager receive emitted light could be specified such that a bandwidth or other time-dependent property of a signal produced and/or detected by light-sensitive elements of the imager (e.g., a rate of speckle events detected by light-sensitive elements of the imager) is within some specified limit(s). For example, the specified region could be a region of biological tissue having a diameter or other characteristic size between approximately 100 microns and approximately 1 millimeter.

In some examples, the imager could be configured to detect, in light received from a particular portion of a biological tissue, the intensity of received light of first and second different polarizations (e.g., orthogonal linear polarizations, orthogonal circular polarizations). This could include the imager having a particular light-sensitive element configured to receive light from the particular portion that has passed through a polarization filter that can be controlled (e.g., electronically controlled) to specify the direction of the polarization of light that is blocked by the polarization filter. In some examples, the imager detecting light of two different polarizations could include the imager having two neighboring pixels or other light-sensitive elements configured to receive light from the particular portion that has passed through respective polarization filters configured to pass light of the respective different polarizations. In some examples, the imager detecting light of two different polarizations could include the imager having two different light-detectors and/or arrays of light detectors (e.g., cameras) configured to receive light from the particular portion that has passed through a beam splitter or other element(s) configured to provide light of the first polarization to a first light-detector/array of light detectors and to provide light of the second polarization to a second light-detector/array of light detectors. The imager detecting light of two different polarizations could include the imager being configured and/or operated in some other way.

Note that the detection of properties of regions of flowing blood in a portion of subsurface vasculature 307 of an arm 305 based on scattering of coherent illumination by scatterers (e.g., illustrative blood cell 309) in the portion of subsurface vasculature 307 is intended as a non-limiting illustrative example of the detection of properties of regions of flow in environments that scatter light and that include scatterers that have time-dependent properties (e.g., location, orientation) related to flow in the regions of flow (e.g., that move within flows of the regions of flow). For example, the environment could be any tissue of a human (e.g., an ankle, an ear, a neck, a portion of central vasculature, a tumor, a tissue undergoing a surgical intervention and/or exposed during such an intervention) or animal, and the detected properties of the regions of flow could be a depth, location, flow velocity, or other property of a region of any flowing fluid of the human or animal body (e.g., arterial blood, capillary blood, venous blood, lymph, interstitial fluid, stomach or other digestive contents, air in the airways and/or lungs, cerebrospinal fluid).

The environment could be an in vivo biological environment (e.g., a tissue of a living human, animal, plant, etc.) or an in vitro environment. The environment could be a biological sample in a sample container, cuvette, pipette, microscope slide, or other vessel. The environment could be part of a biological or chemical process. For example, the environment could be a fluid in a water treatment process, a fluid in a food or drug preparation process, a lake, stream, or river in a natural environment, or some other environment. In another example, the fluid could be a fluid of a microfluidic assay or other microfluidic device or assembly. The environment could be a liquid, a gel, a solid, or some other phase of matter or combination of phases (e.g., an emulsion). The environment could include biological samples that had been freeze-dried, desiccated, frozen, vaporized, alkalated, or otherwise prepared, including adding the imaging agent (i.e., functionalized nanodiamonds and functionalized magnetic particles) to the environment.

In some examples, systems and methods as described herein could be applied to determine properties of regions of flow within biological tissues that are subject to a surgical intervention. That is, the depth or other properties of regions of flow (e.g., portions of vasculature) could be determined in a portion of biological tissue that has been exposed during a surgical intervention, that contains a target to be ablated, excised, resected, or otherwise manipulated (e.g., that contains a tumor, cyst, epileptic center, or infectious agent), that contains a biological structure to be modified (e.g., an aneurysm to be repaired, a vascular anastomosis to be cauterized, a re-entrant conductive cardiac fiber to be severed), that contains a portion of sensitive tissue (e.g., a portion of eloquent cerebral cortex). In such examples, methods and systems as described herein could be applied to determine properties (e.g., depths, locations) of regions of flow in such biological tissue in order to, e.g., determine a level of perfusion within and/or across the tissue, to determine the location, pattern, width, depth, or other information about vasculature in such a biological tissue, to detect the location of a tumor or other target structure and/or tissue in the biological tissue, or to determine some other information about the biological tissue.

Such determined information could be used to ablate a target (e.g., a tumor whose location has been determined), to avoid damaging a sensitive tissue (e.g., to avoid mechanical or thermal damage to a tissue, to avoid disrupting perfusion of and/or vascular supply to the tissue), to determine a portion a vasculature through which to introduce a drug or other substance, to determine a portion a vasculature from which to extract a blood or other tissue sample, or to accomplish and/or instruct some other application(s). Such determined information could be presented to a human surgeon (e.g., via a heads-up-display, via a control console of a robotic surgical system) to inform the performance of a surgical intervention by the surgeon and/or used to determine the operation of a robotic surgical system (e.g., to automatically or semi-automatically ablate a target tissue at a determined location while avoiding damaging sensitive tissues by, e.g., avoiding inflicting damage to vasculature perfusing such sensitive tissue).

Scatterers in the environment could be discrete particles (e.g., blood cells, other cells, micelles, vacuoles, immiscible globules (e.g., oil globules in water), engineered particles (e.g., quantum dots, PEG particles, microparticles of a conductive, semiconductive, magnetic, or other material)) in the environment, or could be discontinuities within a fluid or other constituent of a region of flow whose properties are being determined (e.g., cavitation bubbles, localized turbulence, high thermal and/or pressure gradients, shock waves). The scatterers could be present in the environment (e.g., cells in blood or other biological fluids, microorganisms, particles of silt, or other scatterers in an environmental fluid (e.g., a stream, a pond)) or could be introduced (e.g., production of cavitation bubbles by application of directed energy and/or mechanical intervention, injection of scattering particles (e.g., functionalized particles) into the bloodstream of a human or animal).

Scatterers in an environment could have one or more properties that can be detected and that are related to one or more properties of the environment. For example, a scatterer could selectively interact with an analyte of interest (e.g., the scatterer could be functionalized with a bioreceptor specific to the analyte) and a drag coefficient or other property of the scatterer could be related to the scatterer binding to the analyte. Thus, detection of the velocity of such an individual scatterer or population of such scatterers, relative to one or more determined and/or detected properties of regions of flow containing the scatterer(s), could enable determination of one or more properties of the analyte (e.g., a concentration of the analyte).

Those of skill in the art will understand the term "scatterer" in its broadest sense and that it may take the form of any natural or fabricated material, a cell, a protein or aggregate of proteins, a molecule, cryptophan, a virus, a micelle, a phage, a nanodiamond, a nanorod, a quantum dot, a single-magnetic-domain crystal of a metal, etc. that can interact with light incident on the scatterer to reflect, refract, diffract, or otherwise scatter the incident light. Scatterers could be naturally present in an environment of interest (e.g., blood cells in a portion of subsurface vasculature) or could be added to the environment of interest. Further, a scatterer may be of any shape, for example, spheres, rods, nonsymmetrical shapes, etc., and may be made of a solid, liquid or gaseous material or combinations thereof.

III. Example Determination of Properties of Regions of Flow in Biological Tissue Systems and methods described herein relate to the detection and/or determination of the location, depth (i.e., distance beneath a surface), flow properties (e.g., a mean flow velocity, a distribution of flow velocities), or other properties of regions of flow in biological tissues and other environments containing scattering elements by illuminating the biological tissue with beams of coherent illumination and detecting one or more properties of light responsively emitted from the tissue (e.g., time-varying patterns of the intensity of light emitted from one or more location of the tissue, of light emitted from a location of the tissue having one or more specified polarizations, or according to some other consideration). For example, the depth of a portion of subsurface vasculature (i.e., a region of blood flow) could be determined. Additionally or alternatively, a mean velocity of blood in such a portion of subsurface vasculature could be determined. Further, detection of properties of responsively emitted light(s) could include detecting an intensity, an amplitude, a polarization, a wavelength, a spectral content, a spectral profile, a center frequency, a width, a shape, or some other property of a peak or other feature of a spectrum of the light at one or more points in time and/or patterns of change over time of such properties using a variety of methods.

In some examples, a power spectral density or other information (e.g., a decorrelation time, an autocorrelation, a relationship between mean light intensities detected during a plurality of different time periods and exposure times of the time periods) relating to the frequency content of light received from a portion of a biological tissue could be determined and used to determine information about a region of flow within the biological tissue. This could include comparing frequency-related information that is determined based on light received from different portions of the biological tissues, based on light at difference wavelengths and/or polarizations, or based on light received from the biological tissue that differs in some other way. Such comparisons could include comparing a magnitude, center frequency, shape, or other properties of a feature (e.g., a peak related to the velocity of blood cells in a flow region) of a determined power spectral density or other determined frequency content; comparing a magnitude, lag time, shape, or other properties of a feature of a determined relationship between detected light intensities and associated exposure times; or comparing some other detected or determined properties of detected first and second lights that differ in some way (e.g., have different directions of linear polarization, are emitted from different portions of the biological tissue) and that are emitted from a biological tissue in response to illumination of the biological tissue by coherent illumination.

A power spectral density or other information related to the frequency content of the time-varying intensity of light received from a biological tissue could be determined in a variety of ways. In some examples, the intensity of the received light could be sampled at a sufficiently high frequency (e.g., at a frequency exceeding approximately 1 megahertz) and a Fourier transform or other calculations could be performed on the samples of the detected light intensity. Additionally or alternatively, the intensity of the light could, during a plurality of periods of time each associated with a respective exposure time, be detected. This could include, during each of the time periods, integrating the intensity of the received light during duration of time corresponding to associated exposure times. Additionally or alternatively, the biological tissue could be illuminated during each of the time periods by a respective pulse of light having a pulse width corresponding to associated exposure times. Such detected light intensities could be related to a filtered (e.g., low-pass filtered) version of a time-varying pattern of constructive and destructive interference in the emitted light (e.g., a time-varying pattern related to motion or other changes of scattering elements in a region of flow within the biological tissue). A relationship between such detected light intensities and the exposure times could be related to an autocorrelation of the time-varying pattern of constructive and destructive interference in the emitted light.

Figure 4A:
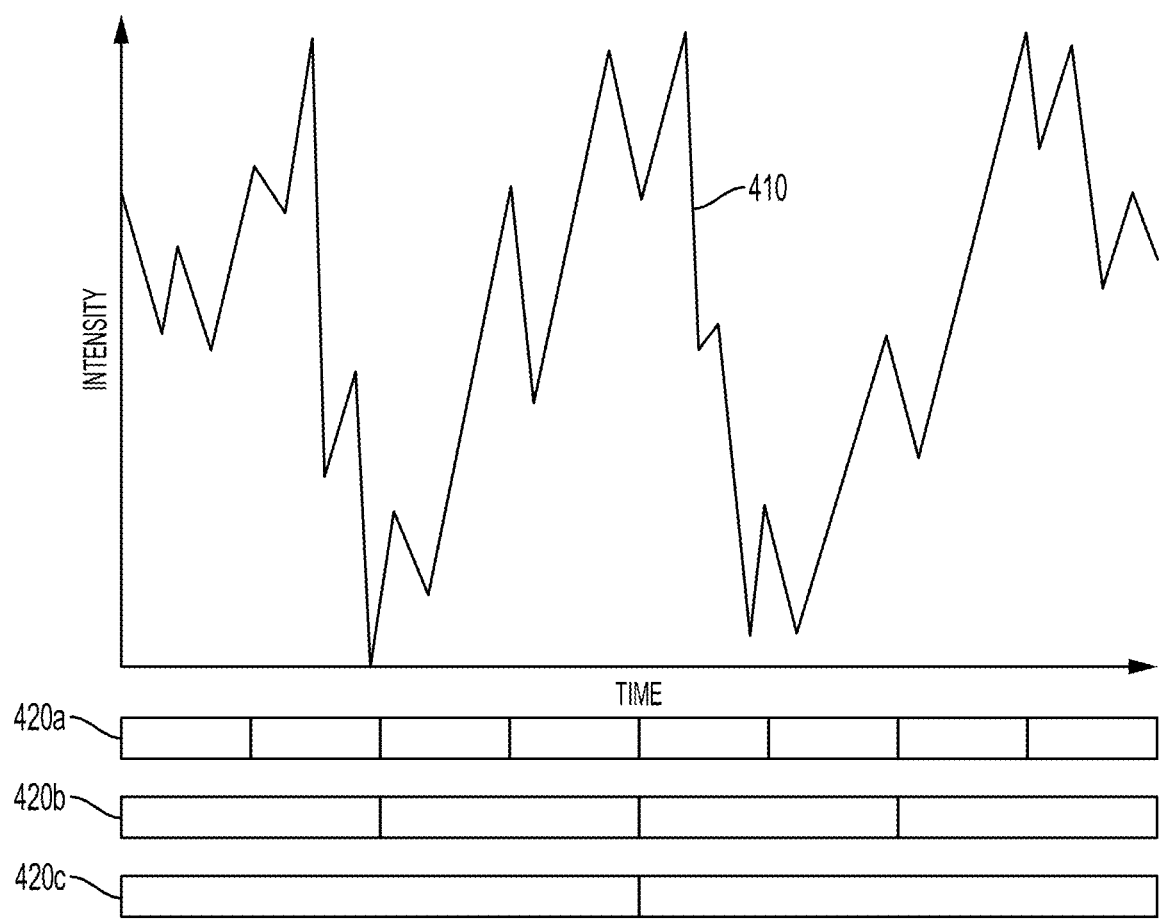
FIG. 4A illustrates an example intensity waveform of light emitted from a biological tissue.

Detecting the intensity of light during a plurality of time periods each associated with a respective exposure time could performed in a variety of ways. FIG. 4A illustrates the time-varying intensity 410 of light emitted from a biological tissue in response to illumination by coherent light. The time-varying intensity 410 varies over time at a variety of different timescales, i.e., contains frequency content across a range of frequencies. The period of time illustrated in FIG. 4A is partitioned into a number of time periods having respective different durations; the timing of these time periods is indicated by 420a, 420b, and 420c.

The time periods illustrated by 420a-c could represent times during which the time-varying intensity 410 of the emitted light could be detected (e.g., time periods during which a light sensor could integrate or otherwise average the intensity of received light). That is, the periods of time indicated by 420a could be associated with a first exposure time that has a duration that is half of the duration of a second exposure time associated with the periods of time indicated by 420b. Further, the first exposure time has a duration that is one quarter of the duration of a third exposure time associate with the periods of time indicated by 420c.

Figure 4B:
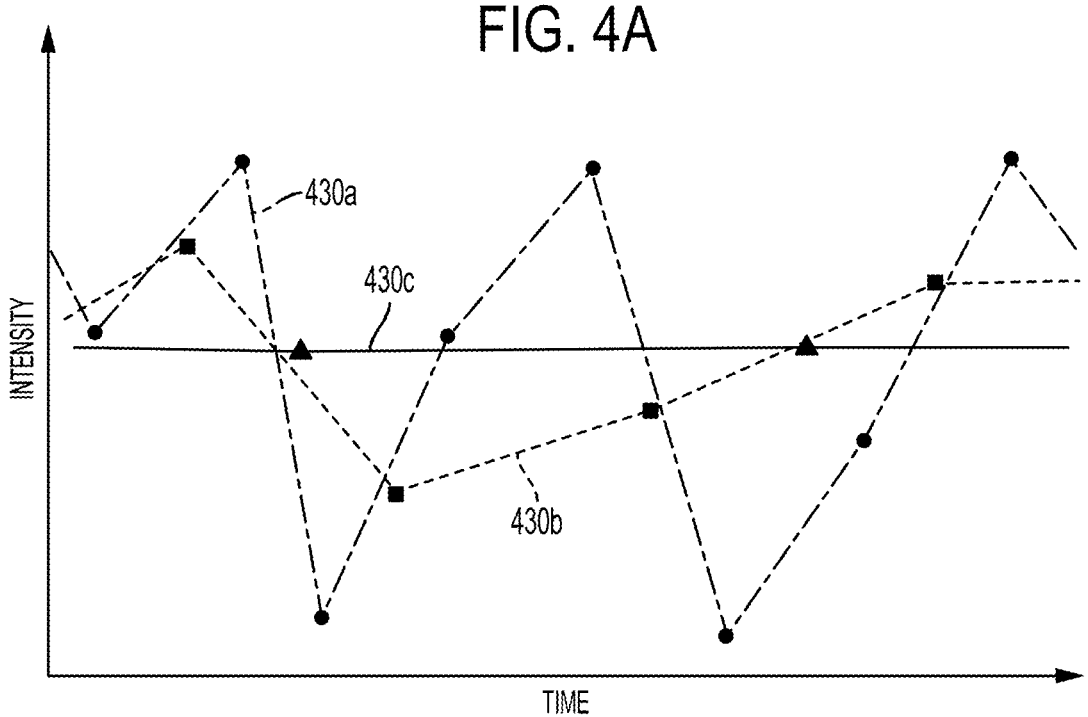
FIG. 4B illustrates example outputs that a system could generate related to the example intensity waveform illustrated in FIG. 4A.

FIG. 4B illustrates light intensities 430a-c of the time-varying intensity 410 of the emitted light that could be detected during the time periods illustrated in FIG. 4A (420a-c, respectively). As illustrated by FIG. 4B, detected light intensities (e.g., 430c) corresponding to longer exposure times (e.g., the third exposure time associated with time periods of 420c) exhibit less variability over time (i.e., less variability between intensities detected during different periods of time associated with the same exposure time, e.g., periods of time indicated by 420c). Thus, light intensities detected during periods of time that are associated with longer-duration exposure times could be related to lower frequency content of the time-varying intensity 410 of light emitted from the biological tissue. Conversely, light intensities (e.g., 430a) detected during periods of time that are associated with shorter-duration exposure times (e.g., 420a) could be related to higher frequency content of the time-varying intensity 410 of light emitted from the biological tissue.

A variety of time periods are illustrated in FIGS. 4A and 4B wherein an exposure time associated with each time period is substantially equal to the duration of the time period, e.g., a light sensor could be operated to detect the integrated or mean intensity of received light during each entire time period. However, a plurality of time periods could be associated with exposure times that have durations that are less than the duration of the respective time periods. For example, a plurality of time periods, each having substantially the same duration, could be associated with respective exposure times having respective different durations that are less than the duration of the time periods. For example, a light sensor could act, during a particular time period, to detect an integrated intensity of a received light during a corresponding particular exposure time having a duration less than the duration of the particular time period.

Additionally or alternatively, a light sensor or other light-sensitive element could act to detect the intensity of received light during the full duration of a particular time period and a light source could be operated to provide a pulse of illumination having a pulse width related to an exposure time that is associated with the particular time period. This could include modulating, over time, an amount of power provided to a light-producing element (e.g., a laser diode, a VCSEL, a pump laser or other cavity-pumping light emitter). Additionally or alternatively, illuminating the environment with a plurality of pulses of light could include operating a shutter (e.g., a liquid crystal shutter), an electronically actuated mirror or other electronically actuated optical element, a rotating wheel, or some other element(s) of a light source to modulate a level of light emitted from a light-emitting element (e.g., a laser) that is used to illuminate the environment.

Further, the duration of the time periods could be different, e.g., a plurality of time periods could have different durations corresponding to respective different time periods (e.g., corresponding to the durations of associated different exposure times). In some examples, the time periods could overlap. For example, the time periods of 420c overlap with the time periods of 420a; first and second different light sensors could detect intensities of received light corresponding to the time periods of 420a and 420c, respectively. Alternatively, a single light sensor could detect intensities during a first plurality of time periods (e.g., 420a) and detected intensities corresponding to a second plurality of time periods that overlap the first plurality of time periods (e.g., 420c) could be determined based on the intensities detected during the first plurality of time periods (e.g., by determining an intensity corresponding to a particular one of the second plurality of time periods related to a time-weighted average of intensities detected during time periods of the first plurality that are overlapped by the particular one of the second plurality of time periods).

Note that multiple intensities of light could be detected from a portion of biological tissue during a particular time period. For example, a light sensor could be a multipixel light sensor (e.g., a CCD camera, an array of CMOS active pixel sensors) and multiple different pixels of the light sensor (e.g., pixels that are proximate each other) could detect light from respective different portions of a biological tissue that are proximate each other. In such examples, a degree of variability between the received light intensities from proximate portions of the biological tissue (e.g., portions of tissue that are emitting light that has one or more properties related to a region of flow beneath the portion of tissue) during a particular time period could be related to an exposure time associated with the particular time period. For example, light intensities detected from a plurality of proximate portions of tissue during a time period that is associated with a longer exposure time could be related to lower frequency content of the time-varying intensity of the received light and thus could exhibit less variability between each other. Conversely, light intensities detected from the plurality of proximate portions of tissue during a time period that is associated with a shorter exposure time could be related to higher frequency content of the time-varying intensity of the received light and thus could exhibit more variability between each other.

A relationship between the detected intensity of light received from a biological tissue (e.g., the intensity of light detected during a plurality of time periods and/or from a plurality of different portions of the tissue) and exposure times associated with the received light could be determined and used, e.g., to determine a depth, location, flow velocity, or other properties of a region of flow within the biological tissue. This could include determining, for each set of detected light intensities associated with a particular exposure time (e.g., by being detected during time period(s) associated with the particular exposure time), a variability between detected light intensities. Such a variability could be determined based on a plurality of intensities detected from light received during a plurality of different times from a particular portion of biological tissue (e.g., from a particular pixel of a multipixel light sensor). Additionally or alternatively, such a variability could be determined based on a plurality of intensities detected from light received during one or more time periods from a plurality of proximate portions of biological tissue (e.g., from a set of proximate pixels of a multipixel light sensor).

Variability of a set of detected light intensities (e.g., light intensities detected from a plurality of portions of tissue and/or during a plurality of different time periods associated with a particular exposure time) could be calculated in a variety of ways. In some examples, a calculated variability could be related to a standard deviation or other measure of variation of the set of intensities divided by or otherwise scaled based on a mean of the set of intensities. Alternatively, a standard deviation or other measure of variation of the set of intensities could be divided by or otherwise scaled based on a mean intensity of light received from the biological tissue determined through some other means. For example, a standard deviation or other measure of variation of intensities detected by a specified set of pixels of a multipixel light sensor could be divided by or otherwise scaled based on a mean intensity of light received from all of the pixels of the multipixel light sensor. In some examples, a standard deviation, mean, and/or other calculations used to determine a variability of detected intensities could be weighted, e.g., different intensities of a set of intensities (e.g., intensities corresponding to pixels that are closer to the center of a specified set of proximate pixels) could contribute more to a standard deviation, mean, or other calculation.

A determined amount of variation between a set of detected light intensities can be referred to as a 'contrast' calculated over a specified spatial (e.g., a set of intensities of light from proximate portions of a tissue detected by corresponding proximate pixels of a multipixel light sensor) and/or temporal (e.g., a set of intensities of light from a particular pixel of a multipixel light sensor that are detected during a plurality of different time periods associated with a particular exposure time) domain. For example, a contrast could be calculated for a particular portion of biological tissue based on light intensities detected by a range of pixels of a multipixel light sensor that are proximate a pixel corresponding to the particular portion of tissue (e.g., based on light intensities detected by a seven-by-seven array of pixels centered on the corresponding pixel). Additionally or alternatively, a contrast could be calculated for a particular portion of biological tissue at a particular point in time based on light intensities detected by one or more pixels of a multipixel light sensor (e.g., a pixel corresponding to the particular portion of tissue and/or pixels proximate such a pixel) during a plurality of time periods before and after the particular point in time (e.g., based on light intensities detected during 21 time periods that are temporally proximate the particular point in time).

Figure 5A:
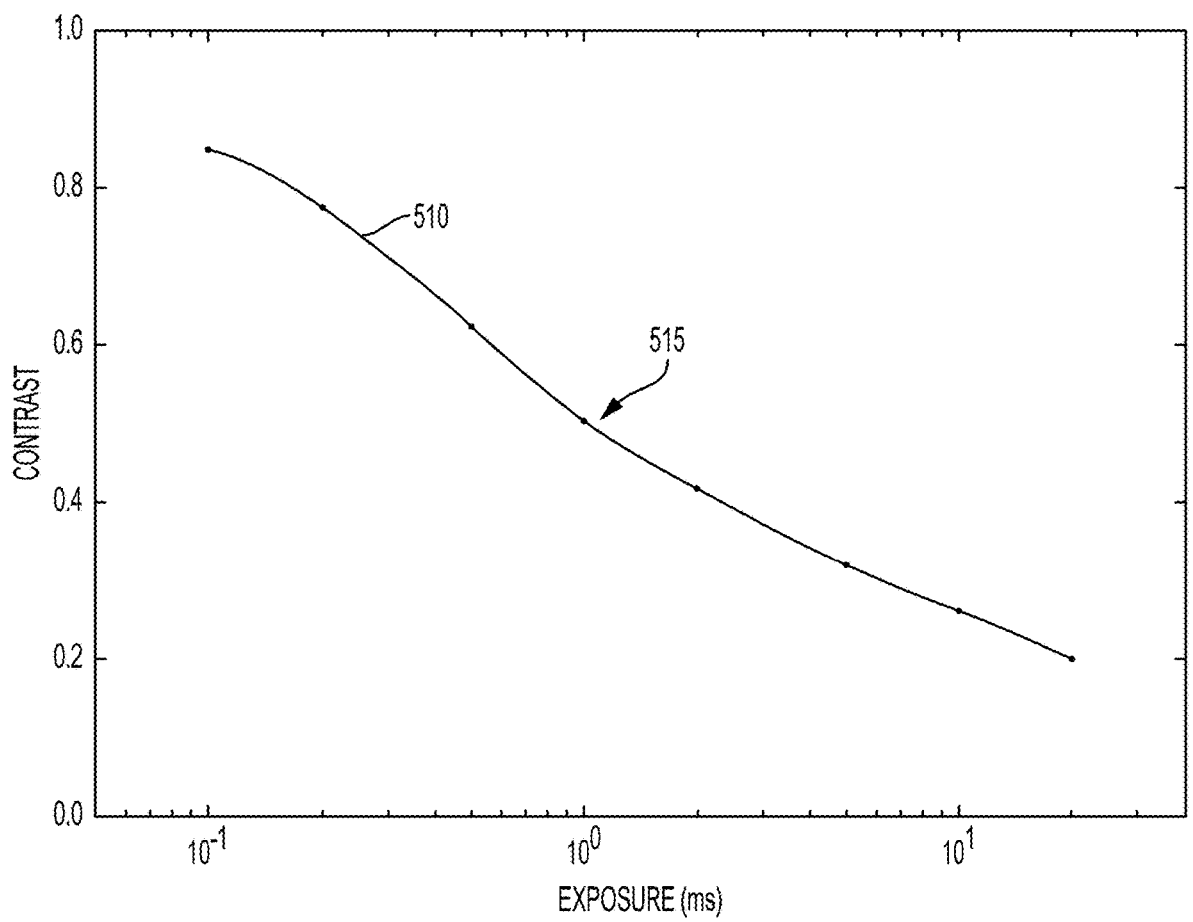
FIG. 5A illustrates a determined relationship between contrast values determined based on light received from a biological tissue and exposure times of the received light.

A plurality of such contrast values or other calculated measures of variability in detected light intensity could be computed, for a particular portion of tissue at a particular point in time, corresponding to a plurality of different exposure times (e.g., based on corresponding pluralities of detected light intensities detected during time periods associated with each of the different exposure times). Determining a relationship between detected intensities of light and exposure times could include determining such a contrast value for each of a set of exposure times, e.g., a set of exposure times spanning a range of exposure times (e.g., a range of exposure times that includes one or more expected decorrelation times of light received from a region of flow within a tissue and related to the flow velocity or other properties of the region of flow). FIG. 5A shows an example relationship 510 between exposure times and intensities of light received from a portion of biological tissue in response to illumination by coherent light. In the example shown in FIG. 5A, the relationship 510 is a set of contrast values determined for each of a set of exposure times. Each contrast value is determined based on a variability of light intensities detected from the portion of biological tissue (e.g., a portion of biological tissue containing a region of flow) and/or from proximate portions of the tissue during one or more time periods associated with a respective exposure time.

Information about a region of flow on or within a biological tissue could be determined directly from such a relationship 510. In some examples, one or more features (e.g., a maximum slope and/or an inflection point of a curve defined by the determined relationship 510, e.g., 515) could be determined from the relationship and used to determine a depth, flow velocity, or other properties of a region of flow within the biological tissue. For example, an inflection point 515 could be detected and one or more properties of the region of flow could be determined based on properties of the inflection point 515. For example, an exposure time corresponding to the inflection point 515 (e.g., an exposure time corresponding to the center or to some other property of the inflection point 515 or of some other feature of the determined relationship 510) could be related to a decorrelation time of the time-varying waveform of the light intensity received from the tissue. Such a decorrelation time could be inversely related to a flow velocity (e.g., a velocity of blood cells) within a region of flow. Further, a shape of the relationship 510 near the inflection point 515 could be related to a distribution of velocities or other properties of the region of flow. Such properties of the region of flow could be determined based on the inflection point 515, e.g., by fitting a parameterized function to the determined relationship 510 at the inflection point 515. A plurality of such parameterized functions could be fitted to the determined relationship 510 and/or other features could be determined corresponding to respective different regions of flow within a biological tissue, e.g., corresponding to respective different portions of subsurface vasculature at respective different depths within the tissue and/or containing blood flowing at respective different flow velocities.

Figure 5B:
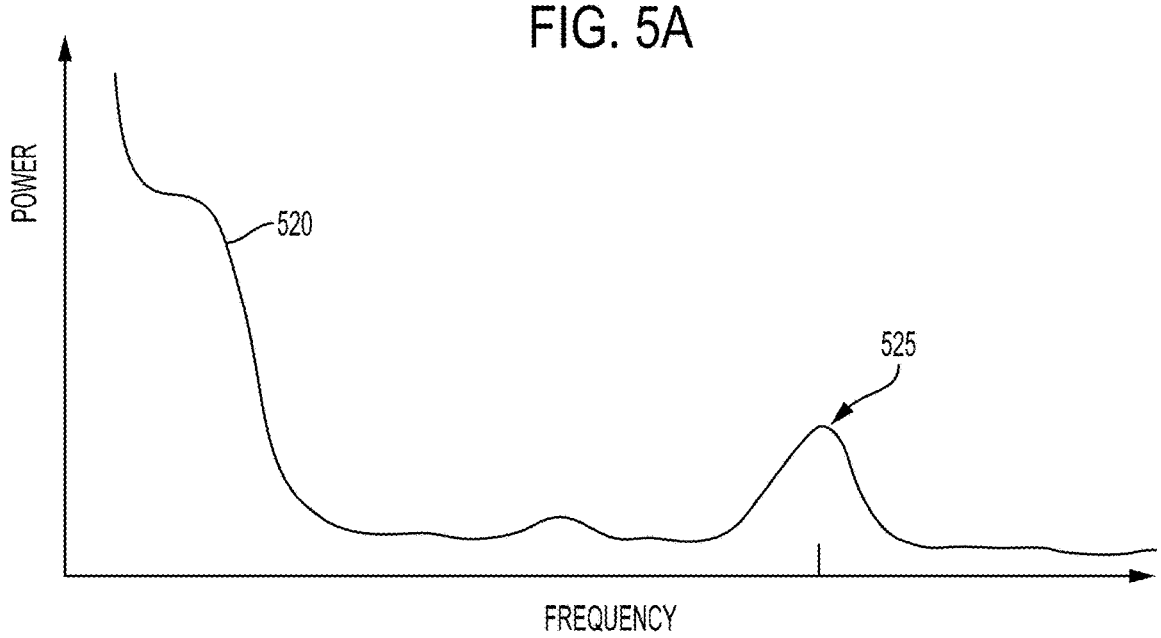
FIG. 5B illustrates example frequency content of the received light determined based on the determined relationship illustrated in FIG. 5A.

Additionally or alternatively, a power spectral density or other frequency information could be determined based on a determined relationship (e.g., 510) between exposure times and intensities of light received during a plurality of time periods associated with such exposure times. FIG. 5B shows an example power spectral density 520 (PSD) of the time-varying waveform of light received from the portion of biological tissue that is related to the determined relationship 510 of FIG. 5A. Features of the PSD 520 could be related to features of the determined relationship 510, e.g., a peak 525 of the PSD 520 could be related to the inflection point 515 of the determined relationship 510. This could include a center frequency of the peak 525 being related (e.g., inversely related) to a decorrelation time of the inflection point 515. Properties of a peak (e.g., 525) in a PSD (e.g., 520) could be related to properties of a corresponding region of flow within biological tissue. For example, a center frequency, width, shape, or other properties of such a peak could be related to a mean flow velocity, a distribution of flow velocities, or other properties of the region of flow. A magnitude of a peak could be related to an amount of light received from the region of flow. Such a magnitude could be related to the depth of the region of flow within the biological tissue. For example, a peak corresponding to a deeper region of flow could have a lower magnitude related, e.g., to absorption and/or scattering of light that has interacted with the region of flow by regions of the biological tissue that are intervening between the region of flow and the surface of the biological tissue.

A PSD (e.g., 520) could be determined from a determined relationship between exposure time and contrast of light received from a biological tissue, or from some other determined relationship between detected intensities of received light and exposure times associated with the received light. For example, one or more samples of a PSD could be determined based on a transform of a determined relationship between contrast and exposure time. Additionally or alternatively, one or more features or subsections of a PSD and/or properties thereof (e.g., a center frequency, width, shape, magnitude, or other properties of a peak in the PSD) could be determined based on a determined relationship between contrast and exposure time, e.g., by fitting a parametric function to one or more features of the determined relationship between contrast and exposure time (e.g., to one or more inflection points or other features within the determined relationship). A PSD could include more than one peak or other feature related to respective one or more regions of flow within a biological tissue (e.g., to regions of blood flow within respective one or more portions of subsurface vasculature). Such one or more features could be detected (and properties thereof) determined based on a detected PSD and/or related features of some other determined information (e.g., inflection points of a determined relationship between exposure times and contrast of light intensity detected during time periods associated with the exposure times).

Properties of a region of flow (e.g., a depth, a flow velocity) could be determined based on a relationship between exposure times and detected intensities of light received from portions of a biological tissue that are proximate the region of flow. Additionally or alternatively, such information could be based on multiple such relationships determined based on light received from respective multiple portions of the biological tissue (e.g., a first portion that contains and/or is proximate a region of flow and second regions that does not/is not), light having respective different polarizations (e.g., perpendicular linear, circular, or other polarizations), or based on other differences in the received light and/or differences in determining the multiple relationships. This could include comparing properties of such determined relationships (e.g., comparing a magnitude of a peak, inflection point slope, or other property) to determine a property of a region of flow (e.g., to determine a depth of the region of flow). Additionally or alternatively, a first determined relationship could be used to determine an offset or bias (e.g., to determine a 'baseline' PSD corresponding to a region of a biological tissue that contains substantially no regions of flow) that could be used to modify a second determined relationship (e.g., to remove a first baseline PSD from a determined second PSD to determine a third PSD that contains information and/or features related substantially only to regions of flow).

FIG. 6A illustrates an example biological tissue 600 including a surface blood vessel 601a disposed on and/or proximate to the surface of the biological tissue 600 (i.e., containing regions of blood flow having a depth of substantially zero) and deep blood vessel 601b located within the biological tissue 600 (i.e., containing regions of blood flow having a depth that is greater than the depth of regions of flow within the surface vessel 601a). For the purposes of illustration, a flow rate of blood within the surface vessel 601a is substantially equal to a flow rate of blood in the deep vessel 601b (illustrated by the arrows within the vessels 601a, 601b). The biological tissue 600 could be illuminated by a beam of coherent illumination and the intensity of light detected from one or more portions of the biological tissue (e.g., first 605a, second 605b, or third 605c portions) during a plurality of time periods associated with respective exposure times could be detected to determine properties (e.g., depths, flow velocities) of regions of flow within the biological tissue 600 as described herein.

A depth, flow properties, or other properties of a region of flow within a biological tissue could be determined based on the detected intensities of light received from the biological tissue at first and second linear polarizations in response to illumination of the biological tissue by coherent, linearly polarized light. This could be related to the effect on the polarization of the illumination by interaction with (e.g., scattering by) elements of the biological tissue (e.g., blood cells). Polarized light that is scattered can have a direction of polarization that is changed from the direction of polarization of the light before being scattered. As a result, light that has interacted with (i.e., been scattered by) scatterers or other elements in deeper regions of a tissue (e.g., deeper regions of flow within a tissue) can be less polarized (e.g., include similar amounts of linearly polarized light of first and second orthogonal linear polarizations) related to an increased number of interactions with the tissue (e.g., with intervening regions of the tissue between a surface of the tissue and a deeper region of flow). A degree of polarization of light received from biological tissue (e.g., a degree of polarization of light that is received from and/or that has interacted with a particular region of flow within the tissue) could be detected and used to determine a depth or other information about elements of the biological tissue (e.g., a depth of the particular region of flow within the tissue).

As an illustrative example, FIG. 6B shows first 610a and second 610b power spectral densities (PSDs) determined based on detected intensities of light having respective first and second linear polarizations that are received from a first portion 605a of the biological tissue in response to illumination of the biological tissue by coherent, linearly polarized light. The PSDs 610a, 610b are determined based on light that is received from the first portion 605a of the tissue 600 and that has interacted with scattering in a region of flow that is within the surface blood vessel 601a (i.e., a region of flow that has a depth within the tissue that is substantially zero). As a result, the first PSD 610a includes a peak 615a related to the flow of blood within the shallow vessel 601a proximate the first portion of tissue 605a while the second PSD 610b includes a corresponding peak having a substantially lesser magnitude, or does not include such a peak. A depth of the region of flow within the surface blood vessel 601a could be determined based on a comparison (e.g., a difference, a ratio) between the magnitude or other property of the peak 615a within the first PSD 610a and properties of a corresponding point or other feature of the second PSD 610b.

In another illustrative example, FIG. 6C shows first 620a and second 620b power spectral densities (PSDs) determined based on detected intensities of light having respective first and second linear polarizations that are received from a second portion 605b of the biological tissue in response to illumination of the biological tissue by coherent, linearly polarized light. The PSDs 620a, 620b are determined based on light that is received from the first portion 605b of the tissue 600 and that has interacted with scattering in a region of flow that is within the deep blood vessel 601b (i.e., a region of flow that has a depth within the tissue that is greater than zero). As a result, the first 620a and second 620b PSDs include respective first 625a and second 625b peaks related to the flow of blood within the deep vessel 601b proximate the second portion of tissue 605b. A depth of the region of flow within the deep blood vessel 601b could be determined based on a comparison (e.g., a difference, a ratio) between the magnitudes or some other properties of the peaks 625a, 625b within the PSDs 620a, 620b (e.g., a ratio of the magnitudes of the peaks being substantially equal to one could be determined and used to determine that the depth of the region of flow within the deep vessel 601b is greater than some specified depth within the tissue 600).

The magnitudes of the peaks 625a, 625b within the PSDs 620a, 620b could be approximately the same due to repeated scattering of the linearly polarized coherent illumination by scatterers and other elements within the biological tissue. That is, each instance of scattering of the linearly polarized illumination could cause a change in the polarization of the scattered illumination, relative to the incoming illumination, such that repeated scattering events act to randomize the polarization of light that is responsively emitted from the biological tissue and that has been scattered a plurality of times, e.g., that has interacted with deep structures within the biological tissue (e.g., a deeper region of flow within the deeper vessel 601b). As a result, light received from the biological tissue that has interacted with deep structures (e.g., light that is received from the second portion of tissue 605b and that has interacted with deeper regions of flow within the deep vessel 601b) could include substantially equal amounts of light at the first and second polarization. Conversely, a portion of light that is received from the biological tissue that has interacted with shallow structures (e.g., a portion of light that is received from the first portion of tissue 605a, such portion having interacted with shallower regions of flow within the surface vessel 601a) could remain substantially polarized (e.g., due to having been scattered few times by elements of the biological tissue). As a result, the first PSD 610a includes a peak 615a while the second PSD 610b does not.

A depth, flow properties, or other properties of a region of flow within a biological tissue could be determined based on the detected intensities of light received from multiple different portions or regions of the biological tissue (e.g., regions proximate to and/or containing such regions of flow and other regions that do not contain and/or not proximate to such regions of flow) in response to illumination of the biological tissue by coherent light. This could be related to the effect on the magnitude, power, or other properties of the illumination by interaction with (e.g., absorption and/or scattering by) elements of the biological tissue (e.g., blood cells, mitochondria, melanin, or other chromophores within the tissue). As a result, light that has interacted with (i.e., been scattered by) scatterers or other elements in deeper regions of a tissue (e.g., deeper regions of flow within a tissue) can have a lower magnitude and/or power related to an increased amount of absorption and/or scattering by the tissue (e.g., with intervening regions of the tissue between a surface of the tissue and a deeper region of flow). A magnitude or power of light received from biological tissue that is received from and/or that has interacted with a particular region of flow within the tissue could be detected and used to determine a depth or other information about elements of the biological tissue (e.g., a depth of the particular region of flow within the tissue).

As an illustrative example, FIG. 6D shows first 630a, second 630b, and third 630c power spectral densities (PSDs) determined based on detected intensities of light that are received from the first 605a, second 605b, and third 605c portions, respectively, of the biological tissue in response to illumination of the biological tissue by coherent light. The PSDs 630a, 630b are determined based on light that is received from the first 605a and second 605b portions of the tissue 600 and that has interacted with scatterers in regions of flow that are within the blood vessels 601a, 601b, respectively. The third PSD 630c is determined based on light that is received from the third 605c portion of the tissue 600 and that has substantially not interacted with regions of blood flow within the blood vessels 601a, 601b. As a result, the first 630a and second 630b PSDs include peaks at the indicated frequency 635 that are related to the flow of blood within the blood vessels 601a, 601b proximate the first 605a, and second 605b portions of tissue, respectively, while the magnitude of the third PSD 630c at the indicated frequency 635 is substantially less than the magnitudes of the first 630a and second 630b PSDs at the indicated frequency 635. A depth of respective regions of flow within respective blood vessels 601a, 601b could be determined based on a comparison (e.g., a difference, a ratio) between the magnitude or other property of the first 630a and second 630b PSDs and properties of a corresponding point or other feature of the third PSD 630c at the indicated frequency 635.

The third PSD 630c could be related to properties of a background level of time-variation in light received from the biological tissue 600 and could be subtracted or otherwise removed from (e.g., by acting a scaling factor, a normalization factor, an offset, or some other form of baseline) the first 630a and second 630b PSDs. As an illustrative example, FIG. 6E shows first 631a and second 631b offset power spectral densities (PSDs) determined by removing the third PSD 630c from the first 630a and second 630b PSDs, respectively. As a result, the first 631a and second 631b offset PSDs include information related to the motion of scatterers in regions of flow (e.g., regions within blood vessels 601a, 601b) proximate the first 605a and second 605b portions of the tissue, respectively. A depth of regions of flow within the shallow 601a and deep 601b blood vessels could be determined based on a magnitude or other property of respective peaks within the offset PSDs 631a, 631b at the illustrated frequency 635 corresponding to blood flow within the blood vessels 601a, 601b.

Note that the determined PSDs and features thereof illustrated in FIGS. 6B-E are intended as non-limiting examples to illustrate methods and systems described herein. Further, a depth or other properties (e.g., a flow velocity) of regions of flow within biological tissues could be determined based on some other determined relationships between exposure times and intensities of light detected from the biological tissue during periods of time associated with such exposure times (i.e., some determined relationships alternative to and/or in addition to power spectral densities determined from such detected intensities of light). In some examples, a determined relationship between a spatial and/or temporal contrast of detected intensities of light and associated exposure times could be used to determine the depth of other properties of regions of flow within a biological tissue. For example, a slope, a second derivative, or some other property of a detected feature of a determined relationship between exposure times and detected light intensities and/or one or more parameters of a parametric curve fitted to such a determined relationship could be used to determine a depth, flow velocity, or other properties of a region of flow within a biological tissue. Additional methods for determining flow properties in a biological environment based on such received lights are anticipated.

Determining a depth, location, flow property (e.g., flow velocity, distribution of flow velocities), or other properties of a region of flow in a biological tissue (or some other environment of interest) could include determining such information (e.g., a depth of a region of flow) for a plurality of volumes, areas, or other regions of the biological tissue. For example, the depth of one or more regions of flow beneath a surface of a biological tissue could be determined for a plurality of locations across an area of biological tissue, e.g., at a plurality of points having a regular spacing across the biological tissue. Such points could correspond to a plurality of portions of the biological tissue from which light could be received (e.g., from which a plurality of intensities of light could be detected during a corresponding plurality of time periods, each time period associated with a respective exposure time).

Determining a depth or other properties of regions of flow within a biological tissue at such a regular or otherwise spaced set of points of a biological tissue could allow for the determination of a map of vasculature or other structures within the biological tissue. For example, such a determined map of depths or other properties of regions of flow could be used to generate a map of blood vessels within the tissue or some other information about the tissue and/or vasculature therein. For example, the depth of blood vessels, depth of regions of greater flow, flow rate pulsatility, blood cell oxygenation, or some other information could be mapped across and/or within the biological tissue. Further, such maps or other information about regions of flow within and/or across the biological tissue could be used to determine the location, pattern, extent, depth beneath a surface of the biological tissue, or other properties of tissues, structures, or other elements within the biological tissue. Such maps could be two-dimensional (e.g., indicating the depth beneath the surface or other information about vasculature or other regions of flow within a biological tissue relative to the surface of the biological tissue) or three-dimensional (reporting the trajectories and other information about the location and extent of vasculature throughout a volume of biological tissue).

Such determined maps or other information describing the depth, location, or other properties of vasculature in a biological tissue could be used in a variety of applications. A determined map of vasculature could be used to avoid damaging vasculature of a tissue when performing a surgical intervention in the tissue. For example, a surgeon and/or robotic surgical system could avoid ablating vasculature of a biological tissue when operating to ablate a target tissue (e.g., a tumor). Additionally or alternatively, a surgical plan could be determined based on a map of the vasculature to avoid disrupting or reducing perfusion to a particular region of tissue, e.g., a nerve, a portion of eloquent cortex, a functional portion of cardiac muscle.

IV. Example Devices

Figure 7:
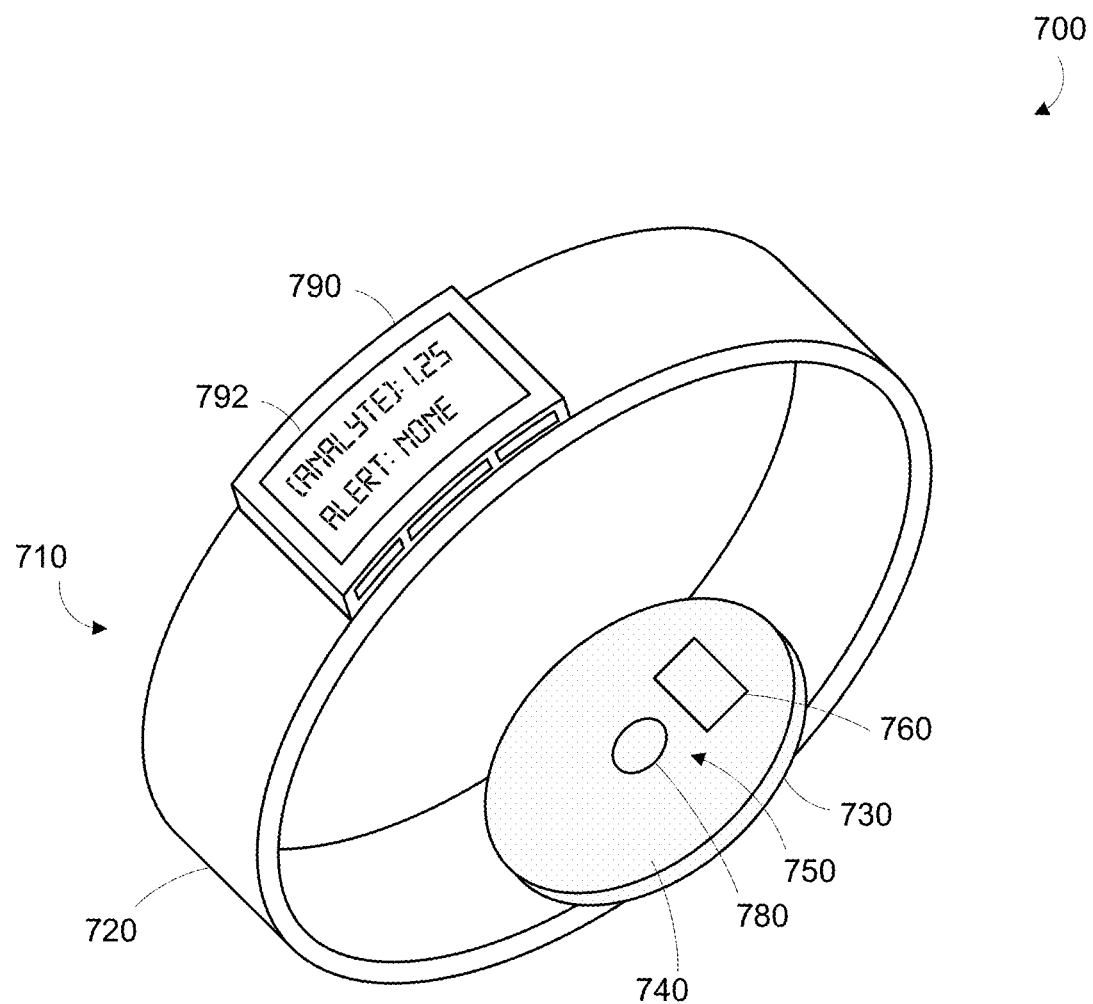
FIG. 7 is a perspective view of an example wearable device.

A wearable device 700 (illustrated in FIG. 7) can automatically measure a depth, location, flow properties (e.g., mean flow velocity, distribution of flow velocities), or other properties of regions of flow (e.g., regions of flow of blood in portions of subsurface vasculature) within the body of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature or other regions of flow within the body are easily observable, the qualification of which will depend on the type of detection system used. The device may be placed in close proximity to the skin or tissue, but need not be touching or in intimate contact therewith. A mount 710, such as a belt, wristband, ankle band, etc. can be provided to mount the device at, on or in proximity to the body surface. The mount 710 may prevent the wearable device from moving relative to the body to reduce measurement error and noise. In one example, shown in FIG. 7, the mount 710, may take the form of a strap or band 720 that can be worn around a part of the body. Further, the mount 710 may be an adhesive substrate for adhering the wearable device 700 to the body of a wearer.

A measurement platform 730 is disposed on the mount 710 such that it can be positioned on the body where subsurface vasculature or other regions of flow within or beneath skin are easily observable. An inner face 740 of the measurement platform is intended to be mounted facing to the body surface. The measurement platform 730 may house a data collection system 750, which may include at least a light source 780 configured to emit beams of coherent illumination into the skin. The measurement platform 730 additionally includes a light sensor 760 configured to detect intensities of light received from one or more location of the skin in response to respective first and second (or more) beams of coherent illumination emitted from the light source 580 (e.g., during a plurality of periods of time associated with respective exposure times). In a non-exhaustive list, the light sensor 760 may include one or more of a photodiode, a phototransistor, a photoresistor, an active pixel sensor, a CCD, a camera, a spectrometer, an interferometer, or some other light sensitive element configured to detect an intensity of some other properties of the emitted light. The components of the data collection system 750 may be miniaturized so that the wearable device may be worn on the body without significantly interfering with the wearer's usual activities.

The data collection system 750 may additionally include additional detectors for detecting other physiological parameters, which could include any parameters that may relate to the health of the person wearing the wearable device. For example, the data collection system 750 could include detectors configured to measure blood pressure, pulse rate, respiration rate, skin temperature, etc. In a non-exhaustive list, additional detectors may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

The light source 780 is configured to transmit beams of coherent illumination that can penetrate the wearer's skin into regions of flow (e.g., portions of subsurface vasculature). The transmitted illumination can be any kind of illumination that is benign to the wearer and that results at least in scattering of the beam of illumination to produce light responsively emitted from the body having one or more detectable properties related to flow properties in the portion of subsurface vasculature (e.g., a time-varying pattern of constructive and destructive interference, a wavelength, a spectrum). The wavelength of the beam of coherent illumination could be between approximately 400 nanometers and approximately 1000 nanometers. In some examples, the wavelength of the beam of coherent illumination could be specified relative to a characteristic size or other property of scatterers (e.g., blood cells, cavitation bubbles, natural and/or artificial particles, bubbles or gas or other material having dissimilar optical properties to a surrounding fluid medium) such that the scatterers could scatter the beam of coherent illumination and cause the environment to emit light having time-varying patterns of constructive and destructive interference and/or time-varying patterns of intensity related to the configuration of the environment and/or scatterers (e.g., related to the depth and/or motion of the scatterers within regions of flow within an environment). The wavelength of the beam of coherent illumination could be within a near-infrared (NIR) transparency window of biological tissue (e.g., between approximately 780 and approximately 810 nanometers).

The wearable device 700 may also include a user interface 790 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 790 may include a display 792 where a visual indication of the alert or recommendation may be displayed. The display 792 may further be configured to provide an indication of the measured physiological parameters, for instance, a determined rate of flow of blood in a portion of subsurface vasculature.

Figure 8:
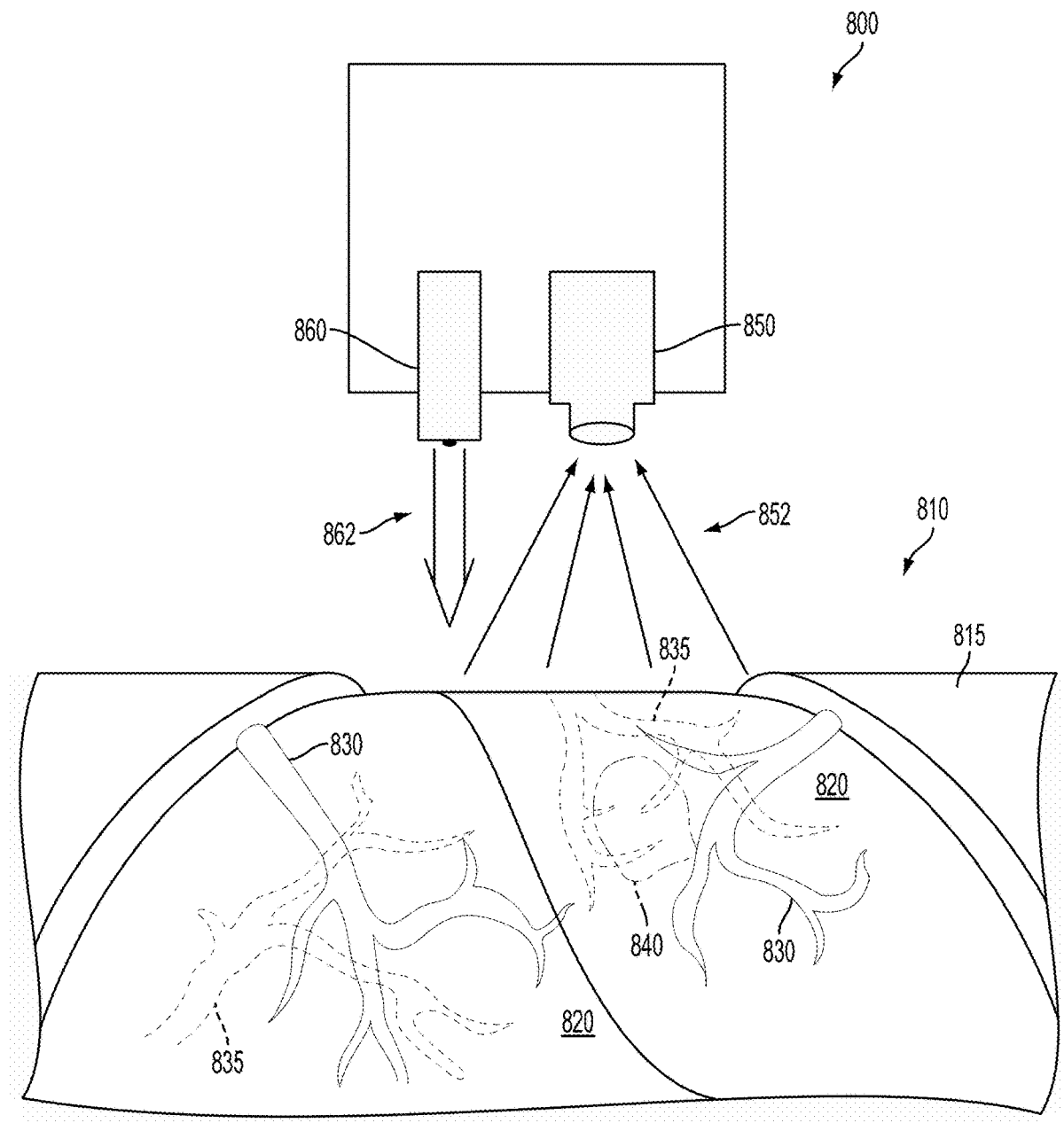
FIG. 8 is a perspective view of an example device, while measuring regions of flow in biological tissue.

A device 800 as illustrated in FIG. 8 can determine a depth, location, flow properties (e.g., a flow rate, a velocity of one or more particles in a fluid flow, or some other properties of flow at and/or through one or more locations or regions) of regions of flow in a biological tissue 810 by emitting coherent illumination 862 into the biological tissue 810 using a light source 860 and detecting one or more properties (e.g., time-varying patterns of constructive and destructive interference, wavelengths, spectra, intensities) of emitted light 852 that is emitted from a plurality of portions (e.g., areas) of the biological tissue 810 in response to illumination by the coherent illumination 862 using an imager 850. The biological tissue 810 can be any environment containing scatterers (e.g., blood cells, other cells, organelles, cell walls, vessel walls) such that the scatterers and other elements of the biological tissue 810 scatter the coherent light 862 in a manner that causes the emitted light 852 to have one or more properties related to properties of regions of flow in the biological tissue 810.

As illustrated in FIG. 8, the biological tissue 810 includes biological tissues undergoing a surgical intervention. The biological tissue 810 includes skin 815 that has been cut and retracted to expose underlying tissues that could be subject to further surgical intervention. The underlying tissues include bulk tissue 820 (e.g., muscle tissue, brain tissue, liver tissue, breast tissue, or some other biological tissue(s)) and a target tissue 840 (e.g., a tumor, neoplasm, cyst, anastomosis, aneurysm, epileptic focus, or some other target of a surgical intervention) within the bulk tissue 820. Surface vessels 830 and deep vessels 835 are present on the surface of and within the bulk tissue, respectively. Depths, flow properties, or other properties of regions of flow within the biological tissue 810 could be detected for surface regions of the biological tissue 810 (e.g., for regions of flow within the surface vessels 830 and/or in interstitial tissue, capillary beds, and/or microvasculature near the surface of the bulk tissue 820) and/or for deeper tissues. Further, the device 800 could be configured to detect depths, locations, flow properties, or other properties of regions of flow through overlying tissues. In some examples, depths, flow properties, or other properties of regions of flow in the bulk tissue 820, vessels 835, 835, and/or target tissue 840 could be detected and/or determined by illuminating and detecting light emitted from such tissues through a layer of overlying tissue such that such flow properties could be detected and/or determined without cutting through and/or retracting the skin 815.

The imager 850 and light source 860 could be configured as illustrated in FIG. 8 (i.e., separate, parallel, non-coaxial) or could be configured in another way, according to an application. In some examples, the imager 850 and light source 860 could be coupled to a set of optical elements to enable some function. In an example, the direction of the beams of coherent illumination 862 emitted by the light source 860 could be controllable using some apparatus, for example a set of galvanometer-driven mirrors. The galvanometers could be operated such that properties of regions of flow beneath and/or proximate to specified areas of the tissue 810 (where the beam from the light source is directed) could be illuminated such that properties of regions of flow beneath and/or proximate to the specified regions could be determined. Other configurations and applications are anticipated.

The imager 850 is configured to detect one or more properties (e.g., time-varying patterns of constructive and destructive interference, wavelengths, spectra, intensities of light during a plurality of periods of time associated with respective exposure times) of light emitted from a plurality of portions of the biological tissue 810 in response to illumination by coherent illumination emitted from the light source 880. In a non-exhaustive list, the imager 850 may include one or more photodiodes, phototransistors, photoresistors, active pixel sensors, CCDs, cameras, angle-sensitive pixels, spectrometers, interferometers, or some other light-sensitive elements configured to detect one or more properties of light emitted from respective portions of the biological tissue 810. The components of the device 800 may be miniaturized so that the device 800 may be used to detect properties of regions of flow in the biological tissue 810 while minimally impeding access to the biological tissue 810, e.g., to cut, ablate, resect, retract, palpate, cauterize, suture, clamp, or otherwise manipulate or interact with the biological tissue 810.

The light source 860 and/or imager 850 could include one or more lenses, filters, collimators, diffraction gratings, or other elements according to an application. For example, the imager 860 could include a filter such that light-sensitive elements of the imager 850 only receive light at wavelengths corresponding to wavelengths of beams of coherent light 862 emitted by the light source 860. In another example, the light source 860 could include a polarizing filter or could be otherwise configured such that the emitted beams of coherent illumination 862 are polarized in a first specified direction. The imager 850 could also include a polarizing filter or other optical element(s) such that one or more light-sensitive elements of the imager 850 individually or in combination can detect a direction and/or degree of polarization of light received from the biological tissue 810.

The light source 860 is configured to transmit a beam of coherent illumination 862 that can penetrate the biological tissue 810, for example, into a lumen of vessels on the surface and/or within the bulk tissue 810. The transmitted illumination can be any kind of illumination that is benign to the biological tissues 820 and that results at least in scattering of the beam of illumination to produce time-varying patterns of constructive and destructive interference in light emitted from the biological tissue (e.g., time-varying intensities of light) that are related to the disposition of scatterers (e.g., blood cells) in regions of flow (e.g., blood flows, interstitial fluid flows) within the biological tissue 810. The wavelength of the beam of coherent illumination could be between approximately 400 nanometers and approximately 1000 nanometers. In some examples, the wavelength of the beam of coherent illumination could be specified relative to a characteristic size or other property of scatterers (e.g., blood cells, cavitation bubbles, natural and/or artificial particles, bubbles or gas or other material having dissimilar optical properties to a surrounding fluid medium) such that the scatterers could scatter the beam of coherent illumination and cause the environment to emit light having time-varying patterns of constructive and destructive interference and/or time-varying patterns of intensity related to the configuration of the environment and/or scatterers (e.g., related to the depth and/or motion of the scatterers within regions of flow within an environment). The wavelength of the beam of coherent illumination could be within a near-infrared (NIR) transparency window of biological tissue (e.g., between approximately 780 and approximately 810 nanometers).

The device 800 could be secured relative to the biological tissue 810 and/or some other tissues and/or surgical instrument(s) in a variety of ways. The components of the device 800 may be disposed on or within a mount or housing or on some other structure for mounting the device 800 to enable stable detection of properties of regions of flow within the biological tissue 810 or other functions relative to elements in a surgical environment, for example, to a surgical frame secured relative to the biological tissue 810 located within a body cavity that is subject to a surgical intervention. The surgical system 800 could include additional components. Device 800 may take a variety of forms, such as a wall, surgical table, ceiling, or floor-mounted device. Device 800 could also take the form of a system, device, or combination of devices that is configured to be part of another device, apparatus, or system. For example, device 800 could take the form of an imager, laser, and/or other components configured to be mounted to or otherwise disposed as part of a surgical apparatus, tool, implement, or system (e.g., a robotic surgical system, a stereotactic surgical apparatus, a laparoscopic and/or endoscopic surgical system). Device 800 could also take the form of a system configured to detect properties of regions of flow in some other industrial environment, medical environment, scientific environment, or some other environment. Device 800 could also take other forms A device as described herein (e.g., 800) could be configured to determine and/or detect properties of regions of flow (e.g., depths, flow velocities) in a biological tissue (e.g., 810) as illustrated herein, or could be configured and/or operated to determine and/or properties of regions of flow in some other environment of interest. The device 800 could be configured to determine properties of regions of flow in a variety of portions/volumes across and/or throughout the biological tissue 810 in order to determine a map of flow throughout the biological tissue 810 (e.g., to determine a flow map of the tissue such that higher flow regions, e.g., vasculature on 830 or within 835 the bulk tissue 820, could be detected, identified, mapped, or otherwise determined). The environment could be an in vivo biological environment (e.g., a tissue of a living human, animal, plant, etc.) or an in vitro environment. The environment could be a biological sample in a sample container, cuvette, pipette, microscope slide, or other vessel. The environment could be part of a biological or chemical process. For example, the environment could be a fluid in a water treatment process, a fluid in a food or drug preparation process, a lake, stream, or river in a natural environment, or some other environment. The environment could be one or more portions of a microfluidic assay, process, or other microfluidic assembly. The environment could include a liquid, a gel, or some other phase of matter or combination of phases (e.g., an emulsion). The environment could include biological samples that had been freeze-dried, desiccated, frozen, vaporized, alkalated, or otherwise prepared, including adding natural and/or artificial scatterers to the environment.

V. Example Electronics Platform for a Device

Figure 9:
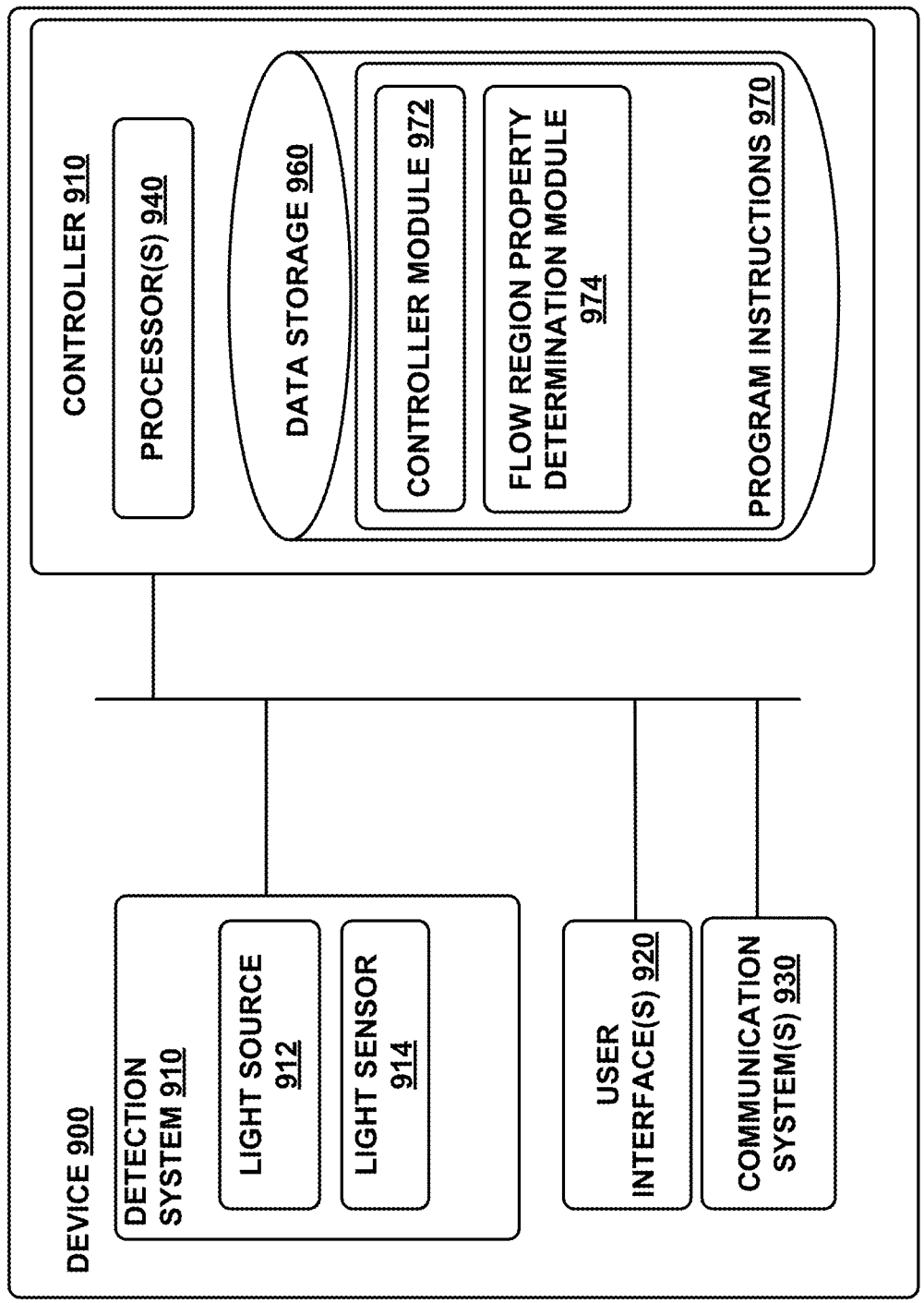
FIG. 9 is a functional block diagram of an example device.

FIG. 9 is a simplified block diagram illustrating the components of a device 900, according to an example embodiment. Device 900 may take the form of or be similar to the devices 100, 300, 700, and 800 shown in FIGS. 1, 3A-C, 7, and 8. In some examples, device 900 could take the form of a device configured to be secured relative to biological tissues undergoing a surgical intervention (e.g., tissue of a human body). For example, the device 900 could be configured to be mounted to a surgical frame, a floor, wall, ceiling, or other structure in a surgical environment or operating room, or secured to some other structure. In some examples, the device 900 could be configured to be secured to and/or a part of an endoscope, laparoscope, thoracoscope, or other surgical instrument configured to be inserted into a body cavity. In some examples, the device 900 could be part of a robotic surgical system and/or could be operated to inform the automated or semi-automated operation of such a system. Additionally or alternatively, the device 900 could be part of a robotic surgical system and information generated by the device could be indicated or otherwise presented to a surgeon or other operator of such a robotic surgical system (e.g., indicated on a display of a control console of such a robotic surgical system) to inform the performance of a surgical intervention by the surgeon. However, device 900 may also take other forms, e.g., could take the form of a device configured to be maintained in proximity to some other environment of interest (e.g., a body part, a biological sample container, a volume of a water treatment system) by a user or operator of the device 900 or by a frame, mount, strap, or other supporting structure (e.g., device 900 could be a body-mountable device). Device 900 could also take the form of a device configured to illuminate and to detect emitted light from an in vitro biological environment or some other environment, for example, a fluid volume within a water treatment process, a microfluidic environment or assay, or some other environment. Device 900 also could take other forms.

In particular, FIG. 9 shows an example of a device 900 having a detection system 910, a user interface 920, communication system(s) 930 for transmitting data to a remote system, and controller 910. The components of the device 900 may be disposed on a mount or on some other structure for mounting the device to enable stable detection of properties of regions of flow in an environment of interest, for example, around a wrist of a wearer such that a portion of subsurface vasculature is visible.

Controller 910 may be provided as a computing device that includes one or more processors 940. The one or more processors 940 can be configured to execute computer-readable program instructions 970 that are stored in the computer readable data storage 960 and that are executable to provide the functionality of a device 900 described herein.

The computer readable data storage 960 may include or take the form of one or more non-transitory, computer-readable storage media that can be read or accessed by at least one processor 940. The one or more computer-readable storage media can include volatile and/or non-volatile storage components, such as optical, magnetic, organic or other memory or disc storage, which can be integrated in whole or in part with at least one of the one or more processors 940. In some embodiments, the computer readable data storage 960 can be implemented using a single physical device (e.g., one optical, magnetic, organic or other memory or disc storage unit), while in other embodiments, the computer readable data storage 960 can be implemented using two or more physical devices.

Detection system 910 includes a light sensor 914 and a light source 912. The light source 912 is configured to emit beams of coherent illumination into an environment of interest (e.g., into a biological tissue). The detection system 910 additionally includes a light sensor 914 configured to detect one or more properties (e.g., a time-varying pattern of constructive and destructive interference, an intensity of light detected during a plurality of periods of time associated with respective exposure times) of light emitted from the environment of interest in response to coherent illumination emitted from the light source 912. In a non-exhaustive list, the light sensor 914 may include one or more of a photodiode, a phototransistor, a photoresistor, an active pixel sensor, a CCD, a camera, a spectrometer, an interferometer, or some other light sensitive element configured to detect one or more properties of the emitted light.

The detection system 910 may additionally include additional detectors for detecting other properties of the environment of interest (e.g., for detecting physiological parameters of a human whose body includes the environment of interest). Such additional detected properties could include any parameters that may relate to the health of the person whose biological tissues are being measured by the device 900. For example, the detection system 910 could include detectors configured to measure blood pressure, pulse rate, respiration rate, skin temperature, etc. In a non-exhaustive list, additional detectors may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

The program instructions 970 stored on the computer readable data storage 960 may include instructions to perform any of the methods described herein. For instance, in the illustrated embodiment, program instructions 970 include a controller module 972 and a flow region property determination module 974.

The controller module 972 can include instructions for operating the detection system 910, for example, the light source 912 and the light sensor 914. In particular, the controller module 972 can include instructions for operating the light source 912 to provide coherent illumination into a target environment during a plurality of time periods, wherein each time period is associated with a respective exposure time. This could include operating the light source 912 to provide the coherent illumination during the entirety of each of the time periods or during a portion of such time periods. In some examples, the light source 912 could provide pulses of coherent illumination during each of the time periods, wherein a duration of each pulse of illumination corresponds to an exposure time associated with the time period during which the pulse of illumination is provided. This could include modulating, over time, an amount of power provided to a light-producing element (e.g., a laser diode, a VCSEL, a pump laser or other cavity-pumping light emitter) of the light source 912. Additionally or alternatively, operating the light source 912 to provide pulses of coherent illumination during each of the time periods could include operating a shutter (e.g., a liquid crystal shutter), an electronically actuated mirror or other electronically actuated optical element, a rotating wheel, or some other element(s) of the light source 912 to modulate a level of light emitted from a light-emitting element (e.g., a laser) that is used to illuminate the environment.

Further, the controller module 972 can include instructions for operating the light sensor 914 to detect the intensity of light received from one or more portions of the environment of interest during each of the plurality of time periods. This could include operating the light sensor 912 to detect the intensity of the received light during the entirety of each of the time periods (e.g., to integrate the intensity of the light received during each of the time periods) or during a portion of such time periods. In some examples, the light sensor 914 could detect the intensity of received light during a specified integration time during each of the time periods, wherein a duration of each integration time corresponds to an exposure time associated with the time period during which the integrated intensity is detected.

The controller module 972 can also include instructions for operating a user interface 920. For example, controller module 972 may include instructions for displaying data collected by the detection system 910 and analyzed by the flow region property determination module 974. Further, controller module 972 may include instructions to execute certain functions based on inputs accepted by the user interface 920, such as inputs accepted by one or more buttons or touchscreen displays disposed on the user interface.

Flow region property determination module 974 may include instructions for receiving data from and/or operating the data collection system 910, analyzing the data to determine a depth, location, flow properties (e.g., flow velocities, mean flow velocities, distributions of flow velocities), or other properties of one or more regions of flow in the environment (e.g., a depth of a region of blood flow within a portion of subsurface vasculature within tissue and/or beneath skin), analyzing such determined properties of the regions of flow to determine a map of vasculature and/or the location and extent of a target tissue, if a medical condition is indicated (e.g., a hemorrhage, a cessation of perfusion to a sensitive tissue), or other analytical processes relating to the environment proximate to the device 900. In particular, the flow region property determination module 974 may include instructions for determining depths of regions of flow within the environment based on determined relationships between intensities of light detected from one or more portions of the environment during a plurality of time periods and exposure times associated with such time periods.

Some of the program instructions of the controller module 972 and the flow region property determination module 974 may, in some examples, be stored in a computer-readable medium and executed by a processor located external to the device 900. For example, the device 900 could be configured to illuminate and to receive light from a portion of biological tissue and then transmit related data to a remote server, which may include a mobile device, a personal computer, the cloud, or any other remote system, for further processing (e.g., for the determination of frequency content of the received light, for determining properties of regions of flow within the biological environment, for determining the location and other information about blood vessels or other structures of the biological environment based on the determined flow properties).

User interface 920 could include indicators, displays, buttons, touchscreens, head-mounted displays, displays of a console of a tele-surgical system, and/or other elements configured to present information about the device 900 to a user and/or to allow the user to operate the device 900. Additionally or alternatively, the device 900 could be configured to communicate with another system (e.g., a cellphone, a tablet, a computer, a remote server) and to present elements of a user interface using the remote system. The user interface 920 could be disposed proximate to the light source 912, light sensor 914, or other elements of the device 900 or could be disposed away from other elements of the device 900 and could further be in wired or wireless communication with the other elements of the device 900. The user interface 920 could be configured to allow a user to specify some operation, function, or property of operation of the device 900. The user interface 920 could be configured to present information about a biological tissue or other contents of a surgical environment (e.g., a map of vasculature, a presence of a target tissue) to the user using a display, to present a determined property of a region of flow within a portion of subsurface vasculature or some other health state of a wearer of the device 900, or to present some other information to a user. Other configurations and methods of operation of a user interface 920 are anticipated.

Communication system(s) 930 may also be operated by instructions within the program instructions 970, such as instructions for sending and/or receiving information via a wireless antenna, which may be disposed on or in the device 900. The communication system(s) 930 can optionally include one or more oscillators, mixers, frequency injectors, etc. to modulate and/or demodulate information on a carrier frequency to be transmitted and/or received by the antenna. In some examples, the device 900 is configured to indicate an output from the controller 910 by transmitting an electromagnetic or other wireless signal according to one or more wireless communications standards (e.g., Bluetooth, WiFi, IRdA, ZigBee, WiMAX, LTE). In some examples, the communication system(s) 930 could include one or more wired communications interfaces and the device 900 could be configured to indicate an output from the controller 910 by operating the one or more wired communications interfaces according to one or more wired communications standards (e.g., USB, FireWire, Ethernet, RS-232).

The computer readable data storage 960 may further contain other data or information, such as scattering, absorption, or other optical properties of tissues of a user of the device 900, that may be useful in determining properties of regions of flow. Further, the computer readable data storage 960 may contain data corresponding to certain tissue optical or other property baselines that describe expected optical or other properties of biological tissues. The baselines may be pre-stored on the computer readable data storage 960, may be transmitted from a remote source, such as a remote server, or may be generated by the flow region property determination module 974 itself. The flow region property determination module 974 may include instructions for generating individual baselines for the user of the device 900 based on data collected over a certain number of measurement periods. For example, the flow region property determination module 974 may generate a baseline tissue scattering and/or absorption spectrum based on detected time-varying patterns of constructive and destructive interference (e.g., time-varying patterns of light intensity) in light received from portions of a biological tissue (e.g., from portions proximate to a portion of vasculature that has been determined and/or that has been indicated, e.g., by a surgeon, to be on the surface of the biological tissue), and store those baselines in the computer readable data storage 960 for later use (e.g., to determine a depth of a portion of vasculature or other region of flow within the biological tissue). Baselines may also be generated by a remote server and transmitted to the device 900 via communication system(s) 930.

In some examples, collected properties of regions of flow, maps of vasculature, or other information generated by the device 900 may additionally be input to a cloud network and be made available for download by a user's physician. Analyses may also be performed on the collected data, such as estimates of post-surgical recovery, determinations of post-surgical treatment or rehabilitation regimens, and/or efficacy of drug treatment regimens, in the cloud computing network and be made available for download by physicians or clinicians. Further, collected information from individuals or populations of device users may be used by physicians or clinicians in monitoring efficacy of a surgical intervention or other treatment.

VI. Illustrative Methods

Figure 10:
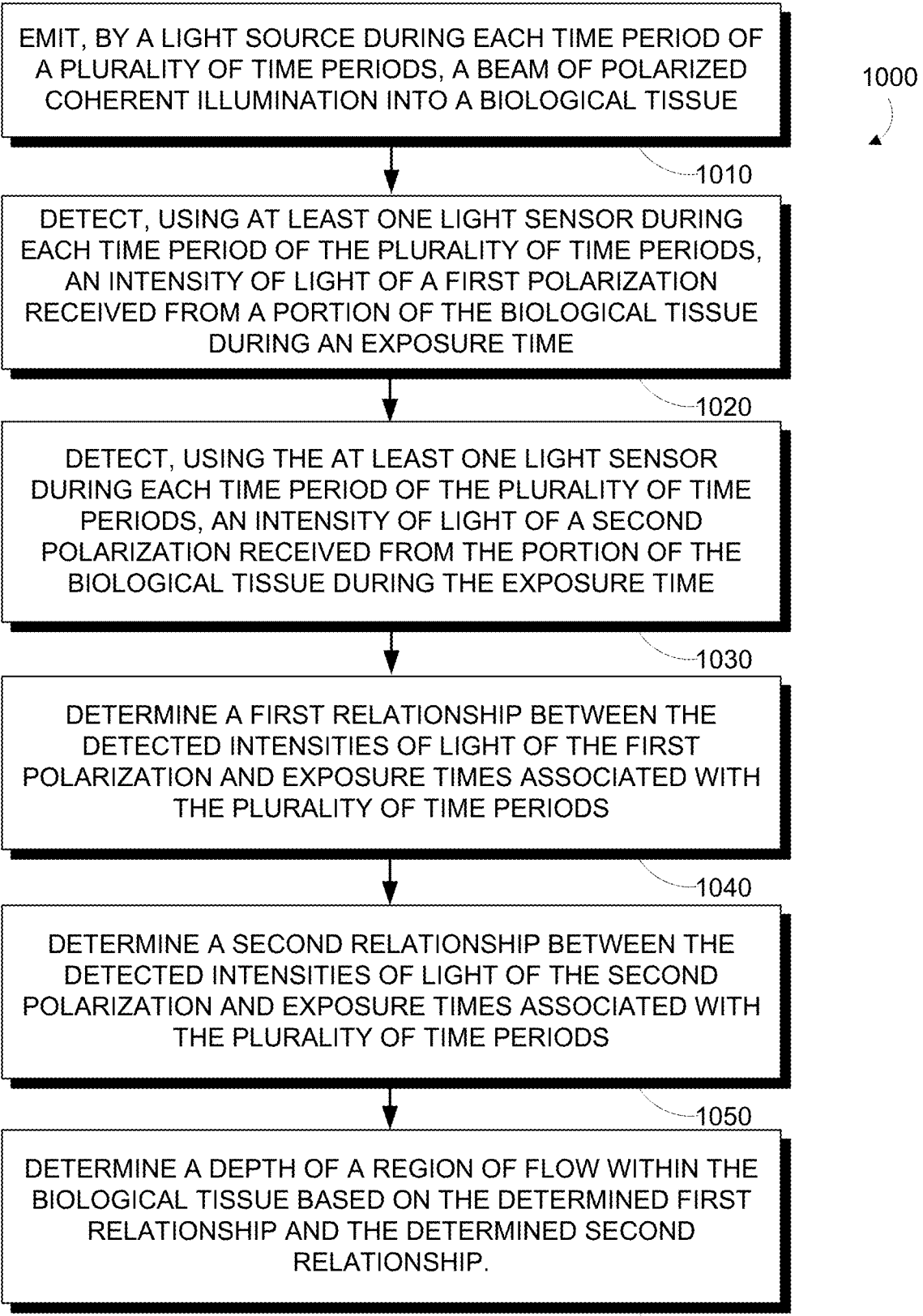
FIG. 10 is a flow chart of an example method

FIG. 10 is a flowchart of a method 1000 for determining the depth of one or more regions of flow within a biological tissue. The method 1000 includes performing a number of steps (i.e., steps 1010, 1020, and 1030) a plurality of times during respective time periods of a plurality of time periods. Each time period of the plurality of time periods is associated with a respective exposure time. The exposure times could all be unique exposure times. Alternatively, sets of time periods of the plurality of time periods could be associated with exposure times that are substantially the same. The time periods could have durations that are substantially the same or could have different durations. The time periods could be sequential and non-overlapping or could overlap (i.e., a first time period could overlap in time and/or be composed of one or more shorter time periods).

The method 1000 includes emitting, by a light source during each time period of the plurality of time periods, a beam of polarized coherent illumination into the biological tissue (1010). This could include operating a laser to emit the beam of coherent illumination. The coherent illumination is such that scatterers and other elements in the biological tissue scatter the coherent illumination such that light is responsively emitted from the biological tissue having one or more properties (e.g., time-varying patterns of constructive and destructive interference, a time-varying intensity) that are related at least to properties (e.g., a depth, a location, flow properties) of regions of flow within the biological tissue. This can include emitting coherent illumination having a specific wavelength, coherence length, or other properties such that the coherent illumination can be scattered by scatterers disposed in the biological tissue, efficiently transmitted through the biological tissue, or other considerations. Illuminating the biological tissue with coherent illumination (1010) can include emitting illumination continuously throughout each of the time periods. Alternatively, illuminating the biological tissue with coherent illumination (1010) can include emitting one or more pulses of illumination during each of the time periods, e.g., emitting one or more pulses of illumination during each time period that have durations corresponding to exposure times associated with each of the time periods.

The method 1000 additionally includes detecting, by at least one light sensor during each time period of the plurality of time periods, an intensity of light of a first polarization received from a portion of the biological tissue during an exposure time (1020). This can include operating a light sensor (e.g., a pixel of a multipixel light sensor) to detect the intensity of light during the full duration of each of the time periods (e.g., during a plurality of integration times that is substantially identical with the timing and duration of the time periods). Alternatively, this (1020) could include operating a light sensor to detect the intensity of the received light during an integration time during a particular time period, where the integration time has a duration corresponding to the exposure time associated with the particular time period. Operating a light sensor to detect the intensity of light during an integration time could include operating an electronic integrator or other analog and/or digital electronic components to integrate an electrical output of a light sensor during the integration time. Additionally or alternatively, the light sensor could include a charge-coupled device that could be operated to have an exposure time corresponding to an integration time.

The method 1000 additionally includes detecting, by the at least one light sensor during each time period of the plurality of time periods, an intensity of light of a second polarization received from the portion of the biological tissue during an exposure time (1030). The first and second polarizations could be orthogonal polarizations (e.g., polarizations that differ by an angle of approximately 90 degrees). Detecting an intensity of light of a second polarization (1030) can include operating the same light sensor and/or light-sensitive element thereof that was used to detect the intensity of light of the first polarization (1020), e.g., by operating a polarization filter to control a polarization of light received from the biological tissue that is provided to the light sensor and/or light-sensitive element thereof. In some examples, detecting an intensity of light of a first polarization (1020) could include operating a first light-sensitive element of the light sensor (e.g., a first pixel that is coupled to a first polarization filter such that the first pixel substantially only receives light of the first polarization from the biological tissue) and detecting an intensity of light of a second polarization (1030) could include operating a second light-sensitive element of the light sensor (e.g., a second pixel that is coupled to a second polarization filter such that the second pixel substantially only receives light of the second polarization from the biological tissue). In some examples, such first and second light-sensitive elements could be pixels of respective different multipixel light sensors (e.g., first and second multipixel CCDs) configured to received light from the biological tissue of the first and second polarizations respectively (e.g., by being coupled to a beam splitter).

The method 1000 additionally includes determining a first relationship between the detected intensities of light of the first polarization and exposure times associated with the plurality of time periods (1040). This could include, for each of the exposure times, determining a contrast value of the light corresponding to a particular exposure time based on light intensities detected during one or more time periods of the plurality of time periods that are associated with the particular exposure time. Determining a first relationship (1040) could include determining a curve or other relationship between such determined contrast values and a range of exposure times. Further, properties of one or more features of such a determined relationship (e.g., a slope, decorrelation time, or other properties of an inflection point in such a relationship) could be determined.

The method 1000 additionally includes determining a second relationship between the detected intensities of light of the second polarization and exposure times associated with the plurality of time periods (1050). This could include, for each of the exposure times, determining a contrast value of the light corresponding to a particular exposure time based on light intensities detected during one or more time periods of the plurality of time periods that are associated with the particular exposure time. Determining a second relationship (1050) could include determining a curve or other relationship between such determined contrast values and a range of exposure times. Further, properties of one or more features of such a determined relationship (e.g., a slope, decorrelation time, or other properties of an inflection point in such a relationship) could be determined.

The method 1000 additionally includes determining a depth of a region of flow within the biological tissue based on the first determined relationship and the second determined relationships (1050). This could include comparing one or more properties of the determined relationship, e.g., comparing a determined property of a feature of the first relationship (e.g., a determined slope of an inflection point within a determined relationship between determined contrasts of the light and corresponding exposure times) to a determined property of a corresponding feature of the second relationship. In some examples, determining a depth of a region of flow within the biological tissue (1050) could include determining a power spectral density or other frequency content from the first and second relationships (e.g., by performing a transformation on a set of determined contrast values of the received light) and comparing such determined power spectral densities or other frequency content.

Figure 11:
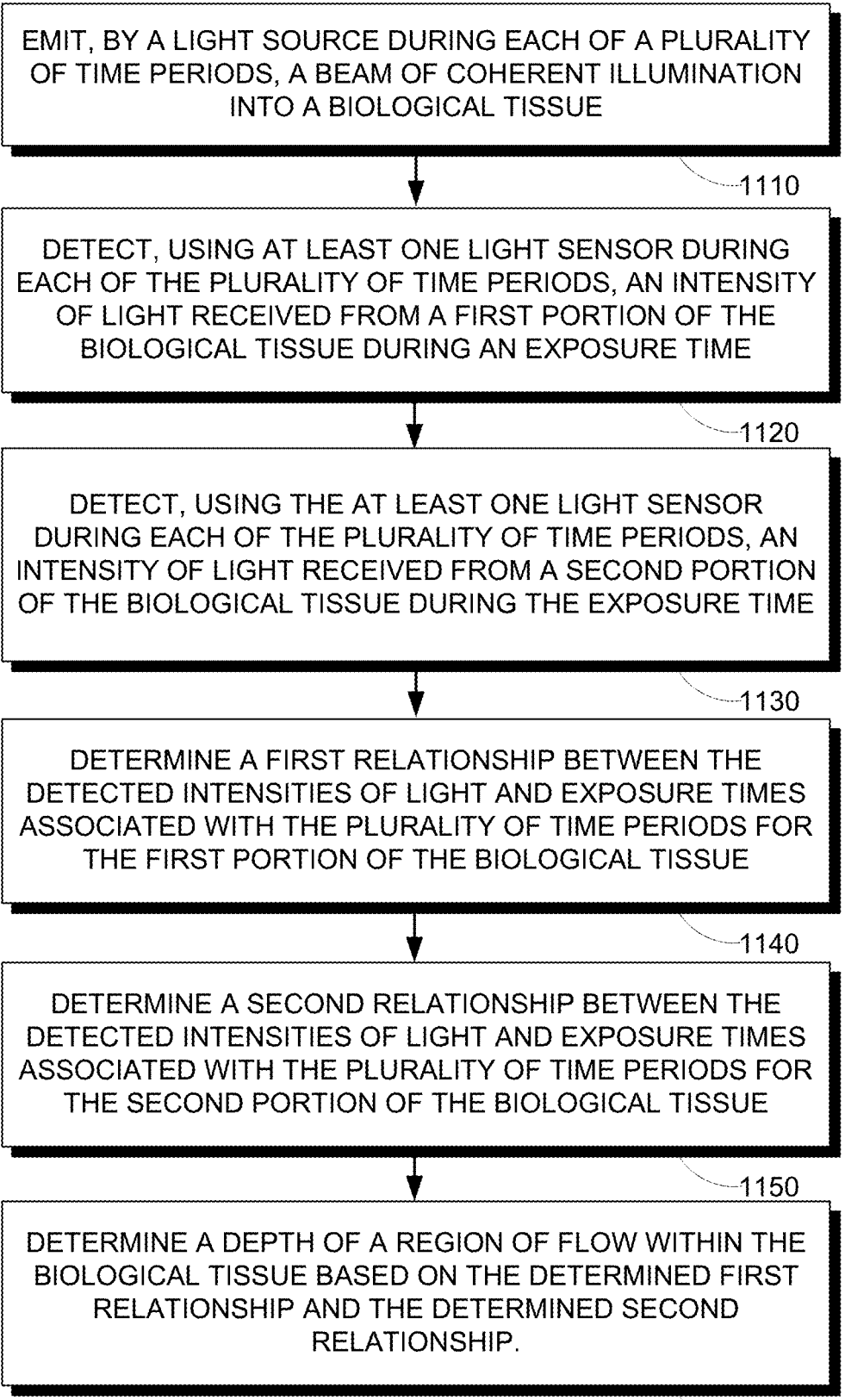
FIG. 11 is a flow chart of an example method.

FIG. 11 is a flowchart of a method 1100 for determining the depth of one or more regions of flow within a biological tissue. The method 1100 includes performing a number of steps (i.e., steps 1110, 1120, and 1130) a plurality of times during respective time periods of a plurality of time periods. Each time period of the plurality of time periods is associated with a respective exposure time. The exposure times could all be unique exposure times. Alternatively, sets of time periods of the plurality of time periods could be associated with exposure times that are substantially the same. The time periods could have durations that are substantially the same or could have different durations. The time periods could be sequential and non-overlapping or could overlap (i.e., a first time period could overlap in time and/or be composed of one or more shorter time periods).

The method 1100 includes emitting, by a light source during each time period of the plurality of time periods, a beam of coherent illumination into the biological tissue (1110). This could include operating a laser to emit the beam of coherent illumination. The coherent illumination is such that scatterers and other elements in the biological tissue scatter the coherent illumination such that light is responsively emitted from the biological tissue having one or more properties (e.g., time-varying patterns of constructive and destructive interference, a time-varying intensity) that are related at least to properties (e.g., a depth, a location, flow properties) of regions of flow within the biological tissue. This can include emitting coherent illumination having a specific wavelength, coherence length, or other properties such that the coherent illumination can be scattered by scatterers disposed in the biological tissue, efficiently transmitted through the biological tissue, or other considerations. Illuminating the biological tissue with coherent illumination (1110) can include emitting illumination continuously throughout each of the time periods. Alternatively, illuminating the biological tissue with coherent illumination (1110) can include emitting one or more pulses of illumination during each of the time periods, e.g., emitting one or more pulses of illumination during each time period that have durations corresponding to exposure times associated with each of the time periods.

The method 1100 additionally includes detecting, by at least one light sensor during each time period of the plurality of time periods, an intensity of light received from a first portion of the biological tissue during an exposure time (1120). This can include operating a light sensor (e.g., a pixel of a multipixel light sensor) to detect the intensity of light during the full duration of each of the time periods (e.g., during a plurality of integration times that are substantially identical with the timing and duration of the time periods). Alternatively, this (1120) could include operating a light sensor to detect the intensity of the received light during an integration time during a particular time period, where the integration time has a duration corresponding to the exposure time associated with the particular time period. Operating a light sensor to detect the intensity of light during an integration time could include operating an electronic integrator or other analog and/or digital electronic components to integrate an electrical output of a light sensor during the integration time. Additionally or alternatively, the light sensor could include a charge-coupled device that could be operated to have an exposure time corresponding to an integration time.

The method 1100 additionally includes detecting, by the at least one light sensor during each time period of the plurality of time periods, an intensity of light received from a second portion of the biological tissue during an exposure time (1130). In some examples, detecting an intensity of light received from a first portion of the biological tissue (1120) could include operating a first light-sensitive element of the light sensor (e.g., a first pixel that is configured to receive light from the first portion of the biological tissue) and detecting an intensity of light received from a second portion of the biological tissue (1130) could include operating a second light-sensitive element of the light sensor (e.g., a second pixel that is configured to receive light from the second portion of the biological tissue).

The method 1100 additionally includes determining a first relationship between the detected intensities of light and exposure times associated with the plurality of time periods for the first portion of the biological tissue (1140). This could include, for each of the exposure times, determining a contrast value of the light corresponding to a particular exposure time based on light intensities detected during one or more time periods of the plurality of time periods that are associated with the particular exposure time. Determining a first relationship (1140) could include determining a curve or other relationship between such determined contrast values and a range of exposure times. Further, properties of one or more features of such a determined relationship (e.g., a slope, decorrelation time, or other properties of an inflection point in such a relationship) could be determined.

The method 1100 additionally includes determining a second relationship between the detected intensities of light and exposure times associated with the plurality of time periods for the second portion of the biological tissue (1150). This could include, for each of the exposure times, determining a contrast value of the light corresponding to a particular exposure time based on light intensities detected during one or more time periods of the plurality of time periods that are associated with the particular exposure time. Determining a second relationship (1150) could include determining a curve or other relationship between such determined contrast values and a range of exposure times. Further, properties of one or more features of such a determined relationship (e.g., a slope, decorrelation time, or other properties of an inflection point in such a relationship) could be determined.

The method 1100 additionally includes determining a depth of a region of flow within the biological tissue based on the first determined relationship and the second determined relationships (1150). This could include comparing one or more properties of the determined relationship, e.g., comparing a determined property of a feature of the first relationship (e.g., a determined slope of an inflection point within a determined relationship between determined contrasts of the light and corresponding exposure times) to a determined property of a corresponding feature of the second relationship. In some examples, determining a depth of a region of flow within the biological tissue (1150) could include determining a power spectral density or other frequency content from the first and second relationships (e.g., by performing a transformation on a set of determined contrast values of the received light) and comparing such determined power spectral densities or other frequency content. In some examples, the first portion of the biological tissue could emit light that has interacted with and/or that otherwise has one or more properties related to the depth of the region of flow (e.g., the first portion could be proximate the region of flow) and the second portion of the biological tissue could emit light that substantially has not interacted with and/or that otherwise is substantially unrelated to the depth of the region of flow (e.g., the second portion could be distant from the region of flow). IN such examples, the second determined relationship and/or properties or information determined therefrom (e.g., a slope of an inflection point, a power spectral density or other frequency information, a magnitude of a peak within such low frequency information) could be used to provide an offset or to otherwise correct corresponding properties or information related to the first determined relationship such that the depth of the region of flow could be determined based on an offset or otherwise corrected version of the first determined relationship.

The methods described above 1000, 1100 could include additional steps or elements in addition to those illustrated in FIGS. 10 and 11, respectively. For example, one or both of the methods 1000, 110 could include determining a map of vasculature in the biological tissue based on determined depths of regions of flow at a plurality of locations of the tissue. One or both of the methods 1000, 1100 could include indicating a determined map of vasculature or other determined information (e.g., flow properties) to a user using a user interface. One or both of the methods 1000, 1100 could include introducing scatterers into the biological tissue (e.g., injecting, ingesting, transdermally transferring, or otherwise introducing the scatterers into a lumen of vasculature of a human). One or both of the methods could include operating a robotic surgical system based on determined depths of regions of flow within the biological tissue. Additional and/or alternative steps of the methods 1000, 1100 are anticipated.

VII. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, depths and/or patterns of vasculature, flow properties, health states, or other information about the user, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to detect depths, flow properties, or other properties of regions of flow within biological tissues of a human body, it is noted that the disclosed devices, systems, and methods can be applied in other contexts as well. For example, detection systems configured to detect properties (e.g., flow rates, locations of regions of flow, a map of flow rates across a volume of the environment) of regions of flow in an environment using coherent light emitters and light sensors as disclosed herein may be included in wearable (e.g., body-mountable) and/or implantable devices. In some contexts, such a detection system is situated to be substantially encapsulated by biocompatible polymeric material suitable for being in contact with bodily fluids and/or for being implanted. In some examples, such detection systems could be incorporated as part of a robotic or otherwise configured surgical system, operated in combination with some other means or method for imaging and/or detecting some other information about biological tissues, or configured and/or operated as part of or in combination with some other system(s).

In other examples, devices, systems, and methods disclosed herein may be applied to measure regions of flow that are not in or on a human body. For example, detection systems disclosed herein may be included devices used to measure regions of flow in a fluid of an animal. In another example, devices, systems, and methods disclosed herein may be applied to measure regions of flow within a natural environment, such as regions of fluid flow in a river, lake, marsh, reservoir, water supply, sanitary sewer system, storm sewer system, or the atmosphere. In another example, devices, systems, and methods disclosed herein may be applied to measure regions of flow that are part of a process, such as a waste treatment process, industrial process, pharmaceutical synthesis process, food preparation process, fermentation process, a microfluidic laboratory or scientific process, or medical treatment process.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A device comprising:
   a light source;
   at least one light sensor; and
   a controller, wherein the controller comprises a computing device programmed to perform operations comprising:
      during each of a plurality of time periods, wherein each time period is associated with a respective exposure time of a set of exposure times:
         emitting, by the light source, a beam of polarized coherent illumination into a biological tissue;
         detecting, using the at least one light sensor, an intensity of light of a first polarization received from a portion of the biological tissue during an exposure time;
         detecting, using the at least one light sensor, an intensity of light of a second polarization received from the portion of the biological tissue during the exposure time;
      determining, for each exposure time in the set of exposure times, a first contrast value and a second contrast value, wherein determining a first contrast value for a given exposure time comprises determining an amount of variation between at least two intensities of light of the first polarization detected during at least two time periods associated with the given exposure time, and wherein determining a second contrast value for the given exposure time comprises determining an amount of variation between at least two intensities of light of the second polarization detected during at least two time periods associated with the given exposure time; and
      determining a depth of a region of flow within the biological tissue as a function of the determined first contrast values and the determined second contrast values.

2. The device of claim 1, further comprising:
   an endoscopic probe configured to be inserted into a body cavity, wherein the light source is configured to emit light from the endoscopic probe, and wherein the at least one light sensor is configured to detect light received from the biological tissue via the endoscopic probe.

3. The device of claim 1, wherein the operations further comprise:
   determining a flow velocity within the region of flow as a function of the determined first contrast values.

4. The device of claim 3, wherein the determined flow velocity is a flow velocity of blood cells in the region of flow.

5. The device of claim 3, wherein determining a flow velocity within the region of flow as a function of the determined first contrast values comprises:
   detecting a feature in the determined first contrast values;
   determining an exposure time corresponding to the detected feature; and
   using the determined exposure time to determine a flow velocity within the region of flow.

6. The device of claim 1, wherein the operations further comprise: during each of the plurality of time periods:
   detecting, using the at least one light sensor, an intensity of light of the first polarization received from a further portion of the biological tissue during an exposure time; and
   detecting, using the at least one light sensor, an intensity of light of the second polarization received from the further portion of the biological tissue during an exposure time;
   determining, for each exposure time in the set of exposure times, a third contrast value and a fourth contrast value, wherein determining a third contrast value for a given exposure time comprises determining an amount of variation between at least two intensities of light of the first polarization received from the further portion of biological tissue detected during at least two time periods associated with the given exposure time, and wherein determining a fourth contrast value for the given exposure time comprises determining an amount of variation between at least two intensities of light of the second polarization received from the further portion of biological tissue detected during at least two time periods associated with the given exposure time;
   determining a depth of a further region of flow within the biological tissue as a function of the determined third contrast values and the determined fourth contrast values; and
   using the determined depths of regions of flow within the biological tissue to generate a map of one or more portions of vasculature in the biological tissue.

7. The device of claim 1, wherein determining a depth of a region of flow within the biological tissue as a function of the determined first contrast values and the determined second contrast values comprises:
  detecting a feature in the determined first contrast values;
  determining an exposure time corresponding to the detected feature;
  determining a ratio between a determined first contrast value corresponding to the determined exposure time and a determined second contrast value corresponding to the determined exposure time; and
  using the determined ratio to determine the depth of the region of flow.

8. The device of claim 1, wherein determining a depth of a region of flow within the biological tissue as a function of the determined first contrast values and the determined second contrast values comprises:
  detecting a feature in the determined first contrast values;
  determining an exposure time corresponding to the detected feature;
  determining a difference between a determined first contrast value corresponding to the determined exposure time and a determined second contrast value corresponding to the determined exposure time; and
  using the determined difference to determine the depth of the region of flow.

9. The device of claim 1, wherein each time period being associated with a respective exposure time comprises the controller operating the at least one light sensor, during each time period, to detect light during an integration time having a duration corresponding to the exposure time of the time period.

10. The device of claim 1, wherein each time period being associated with a respective exposure time comprises the controller operating the light source, during each time period, to emit a pulse of light having a duration corresponding to the exposure time of the time period.

11. A device comprising:
  a light source;
  at least one light sensor; and
  a controller, wherein the controller comprises a computing device programmed to perform operations comprising:
    during each of a plurality of time periods, wherein each time period is associated with a respective exposure time of a set of exposure times:
      emitting, by the light source, a beam of coherent illumination into a biological tissue;
      detecting, using the at least one light sensor, an intensity of light received from a first portion of the biological tissue during an exposure time;
      detecting, using the at least one light sensor, an intensity of light received from a second portion of the biological tissue during the exposure time;
    determining, for each exposure time in the set of exposure times, a first contrast value and a second contrast value, wherein determining a first contrast value for a given exposure time comprises determining an amount of variation between at least two intensities of light received from the first portion of biological tissue detected during at least two time periods associated with the given exposure time, and wherein determining a second contrast value for the given exposure time comprises determining an amount of variation between at least two intensities of light received from the second portion of biological tissue detected during at least two time periods associated with the given exposure time; and
    determining a depth of a region of flow within the biological tissue as a function of the determined first contrast values and the determined second contrast values.

12. The device of claim 11, further comprising:
  an endoscopic probe configured to be inserted into a body cavity, wherein the light source is configured to emit light from the endoscopic probe, and wherein the at least one light sensor is configured to detect light received from the biological tissue via the endoscopic probe.

13. The device of claim 11, wherein the operations further comprise:
  determining a flow velocity within the region of flow as a function of the determined first contrast values.

14. The device of claim 13, wherein the determined flow velocity is a flow velocity of blood cells in the region of flow.

15. The device of claim 13, wherein determining a flow velocity within the region of flow as a function of the determined first contrast values comprises:
  detecting a feature in the determined first contrast values;
  determining an exposure time corresponding to the detected feature; and
  using the determined exposure time to determine a flow velocity within the region of flow.

16. The device of claim 11, wherein the operations further comprise:
  during each of the plurality of time periods:
    detecting, using the at least one light sensor, an intensity of light received from a third portion of the biological tissue during an exposure time; and
    detecting, using the at least one light sensor, an intensity of light received from a fourth portion of the biological tissue during an exposure time;
  determining, for each exposure time in the set of exposure times, a third contrast value and a fourth contrast value, wherein determining a third contrast value for a given exposure time comprises determining an amount of variation between at least two intensities of light received from the third portion of biological tissue detected during at least two time periods associated with the given exposure time, and wherein determining a fourth contrast value for the given exposure time comprises determining an amount of variation between at least two intensities of light of the second polarization received from the fourth portion of biological tissue detected during at least two time periods associated with the given exposure time;
  determining a depth of a further region of flow within the biological tissue as a function of the determined third contrast values and the determined fourth contrast values; and
  using the determined depths of regions of flow within the biological tissue to generate a map of one or more portions of vasculature in the biological tissue.

17. The device of claim 11, wherein determining a depth of a region of flow within the biological tissue as a function of the determined first contrast values and the determined second contrast values comprises:
  detecting a feature in the determined first contrast values;
  determining an exposure time corresponding to the detected feature;

determining a ratio between a determined first contrast value corresponding to the determined exposure time and a determined second contrast value corresponding to the determined exposure time; and using the determined ratio to determine the depth of the region of flow.

18. The device of claim 11, wherein determining a depth of a region of flow within the biological tissue as a function of the determined first contrast values and the determined second contrast values comprises:

detecting a feature in the determined first contrast values;

determining an exposure time corresponding to the detected feature;

determining a difference between a determined first contrast value corresponding to the determined exposure time and a determined second contrast value corresponding to the determined exposure time; and using the determined difference to determine the depth of the region of flow.

19. The device of claim 11, wherein each time period being associated with a respective exposure time comprises the controller operating the at least one light sensor, during each time period, to detect light during an integration time having a duration corresponding to the exposure time of the time period.

20. The device of claim 11, wherein each time period being associated with a respective exposure time comprises the controller operating the light source, during each time period, to emit a pulse of light having a duration corresponding to the exposure time of the time period.

* * * * *